US009924906B2

(12) United States Patent
Lin et al.

(10) Patent No.: US 9,924,906 B2
(45) Date of Patent: *Mar. 27, 2018

(54) RANDOM BODY MOVEMENT CANCELLATION FOR NON-CONTACT VITAL SIGN DETECTION

(71) Applicant: University of Florida Research Foundation, Inc., Gainesville, FL (US)

(72) Inventors: Jenshan Lin, Gainesville, FL (US); Changzhi Li, Lubbock, TX (US); Ya-Chi Liu, Douilou (TW)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/259,580

(22) Filed: Sep. 8, 2016

(65) Prior Publication Data

US 2016/0374622 A1    Dec. 29, 2016

Related U.S. Application Data

(63) Continuation of application No. 14/276,300, filed on May 13, 2014, now Pat. No. 9,447,812, which is a
(Continued)

(51) Int. Cl.
*A61B 5/08* (2006.01)
*A61B 5/00* (2006.01)
(Continued)

(52) U.S. Cl.
CPC .......... *A61B 5/7214* (2013.01); *A61B 5/0205* (2013.01); *A61B 5/05* (2013.01);
(Continued)

(58) Field of Classification Search
CPC ........ A61B 5/05; A61B 5/0507; A61B 5/7214
See application file for complete search history.

(56) References Cited

U.S. PATENT DOCUMENTS

| | | |
|---|---|---|
| 3,796,208 A | 3/1974 | Bloice |
| 4,085,740 A | 4/1978 | Allen, Jr. |

(Continued)

FOREIGN PATENT DOCUMENTS

| | | |
|---|---|---|
| EP | 1058451 | 12/2000 |
| GB | 2099257 | 12/1982 |

(Continued)

OTHER PUBLICATIONS

Xiao et al., Accuracy of a Low-Power Ka-band Non-contact Heartbeat Detector Measured from Four sides of a Human Body, pp. 1576-1579, 2006.*

(Continued)

*Primary Examiner* — Puya Agahi
(74) *Attorney, Agent, or Firm* — Thomas | Horstemeyer LLP; Christopher B. Linder; Randy R. Schoen

(57) ABSTRACT

A method and system for cancelling body movement effect for non-contact vital sign detection is described. The method begins with sending on a first electromagnetic wave transceiver a first electromagnetic signal with a first frequency to a first side of a body, such as a person or animal. Simultaneously using a second electromagnetic wave transceiver a second electromagnetic signal is sent with a second frequency to a second side of a body, wherein the first frequency and the second frequency are different frequencies. A first reflected electromagnetic signal reflected back in response to the first electromagnetic wave on the first transceiver is received and a first baseband complex signal is extracted. Likewise a second reflected electromagnetic signal reflected back in response to the second electromagnetic wave on the second transceiver is received and a (Continued)

second baseband complex signal is extracted. The first baseband complex signal is mathematically combined with the second baseband complex signal to cancel out a Doppler frequency drift therebetween to yield a periodic Doppler phase effect.

20 Claims, 18 Drawing Sheets

Related U.S. Application Data continuation of application No. 12/668,700, filed as application No. PCT/US2008/069766 on Jul. 11, 2008, now Pat. No. 8,721,554.

(60) Provisional application No. 60/949,285, filed on Jul. 12, 2007.

(51) Int. Cl.
| | | |
|---|---|---|
| A61B 5/05 | | (2006.01) |
| G06F 17/14 | | (2006.01) |
| G06F 19/00 | | (2011.01) |
| A61B 5/0205 | | (2006.01) |
| A61B 5/024 | | (2006.01) |

(52) U.S. Cl.
CPC .......... *A61B 5/0507* (2013.01); *A61B 5/6823* (2013.01); *A61B 5/7278* (2013.01); *A61B 5/742* (2013.01); *G06F 17/14* (2013.01); *G06F 19/3418* (2013.01); *A61B 5/024* (2013.01); *A61B 5/0816* (2013.01)

(56) References Cited

U.S. PATENT DOCUMENTS

| | | |
|---|---|---|
| 4,357,944 A | 11/1982 | Mauser et al. |
| 4,378,698 A | 4/1983 | Masse et al. |
| 4,513,748 A | 4/1985 | Nowogrodzki et al. |
| 5,507,291 A | 4/1996 | Stirbl et al. |
| 5,647,834 A | 7/1997 | Ron |
| 5,694,093 A | 12/1997 | DaSilva et al. |
| 5,867,257 A | 2/1999 | Rice et al. |
| 3,006,188 A | 12/1999 | Bogdashevsky et al. |
| 6,064,383 A | 5/2000 | Skelly |
| 6,132,371 A | 10/2000 | Dempsey et al. |
| 6,188,220 B1 | 2/2001 | Schaefer |
| 6,219,657 B1 | 4/2001 | Hatayama |
| 6,275,806 B1 | 8/2001 | Pertrushin |
| 6,480,826 B2 | 11/2002 | Pertrushin |
| 6,697,457 B2 | 2/2004 | Petrushin |
| 6,728,679 B1 | 4/2004 | Strubbe et al. |
| 6,768,938 B2 | 7/2004 | McBrien et al. |
| 6,931,341 B2 | 8/2005 | Wakabayashi et al. |
| 7,043,008 B1 | 5/2006 | Dewan |
| 7,073,384 B1 | 7/2006 | Donskoy et al. |
| 7,116,426 B2 | 10/2006 | Lal et al. |
| 7,138,905 B2 | 11/2006 | Pavlidis et al. |
| 7,165,033 B1 | 1/2007 | Liberman |
| 7,272,431 B2 | 9/2007 | McGrath |
| 7,373,301 B2 | 5/2008 | Kemp et al. |
| 7,401,020 B2 | 7/2008 | Eide |
| 7,451,079 B2 | 11/2008 | Oudeyer |
| 7,477,398 B2 | 1/2009 | Lal et al. |
| 7,606,701 B2 | 10/2009 | Degani et al. |
| 7,627,475 B2 | 12/2009 | Petrushin |
| 7,809,117 B2 | 10/2010 | Runge et al. |
| 7,817,082 B2 | 10/2010 | Dwelly et al. |
| 7,848,896 B2 | 12/2010 | Lin et al. |
| 7,903,020 B2 | 3/2011 | Lin et al. |
| 7,914,468 B2 | 3/2011 | Shalon et al. |
| 8,052,600 B2 | 11/2011 | Beck et al. |
| 8,239,000 B1 | 8/2012 | Morris et al. |
| 8,306,610 B2 | 11/2012 | Mirow |
| 8,652,040 B2 | 2/2014 | LeBoeuf et al. |
| 8,721,554 B2 | 5/2014 | Lin et al. |
| 8,814,805 B2 | 8/2014 | Lin et al. |
| 9,200,945 B2 | 12/2015 | Lin et al. |
| 9,477,812 B2 | 10/2016 | Lin et al. |
| 2002/0002464 A1 | 1/2002 | Petrushin |
| 2002/0007119 A1 | 1/2002 | Pelissier |
| 2002/0065466 A1 | 5/2002 | Rather et al. |
| 2002/0101568 A1 | 8/2002 | Eberl et al. |
| 2002/0139842 A1 | 10/2002 | Swaine |
| 2003/0028384 A1 | 2/2003 | Kemp et al. |
| 2003/0055654 A1 | 3/2003 | Oudeyer |
| 2003/0069728 A1 | 4/2003 | Tato et al. |
| 2003/0093280 A1 | 5/2003 | Oudeyer |
| 2003/0163311 A1 | 8/2003 | Gong |
| 2003/0182117 A1 | 9/2003 | Monchi et al. |
| 2003/0187660 A1 | 10/2003 | Gong |
| 2003/0208113 A1 | 11/2003 | Mault et al. |
| 2004/0039282 A1 | 2/2004 | Szabo et al. |
| 2004/0123667 A1 | 7/2004 | McGrath |
| 2004/0141417 A1 | 7/2004 | Wakabayashi et al. |
| 2004/0167774 A1 | 8/2004 | Shrivastav |
| 2004/0181143 A1 | 9/2004 | Israel |
| 2004/0249258 A1 | 12/2004 | Tupin et al. |
| 2004/0249634 A1 | 12/2004 | Degani et al. |
| 2005/0033127 A1 | 2/2005 | Ciurczak et al. |
| 2005/0073424 A1 | 4/2005 | Ruoss et al. |
| 2005/0088981 A1 | 4/2005 | Woodruff et al. |
| 2005/0128123 A1 | 6/2005 | Greneker et al. |
| 2005/0131273 A1 | 6/2005 | Asano et al. |
| 2005/0154264 A1 | 7/2005 | Lecompte et al. |
| 2005/0163302 A1 | 7/2005 | Mock et al. |
| 2005/0171411 A1 | 8/2005 | KenKnight et al. |
| 2006/0028556 A1 | 2/2006 | Bunn et al. |
| 2006/0058694 A1 | 3/2006 | Clark et al. |
| 2006/0064037 A1 | 3/2006 | Shalon et al. |
| 2006/0122834 A1 | 6/2006 | Bennett |
| 2006/0209631 A1 | 9/2006 | Melese et al. |
| 2006/0224046 A1 | 10/2006 | Ramadas et al. |
| 2007/0066916 A1 | 3/2007 | Lemos |
| 2007/0093702 A1 | 4/2007 | Yu et al. |
| 2007/0149883 A1 | 6/2007 | Yesha |
| 2007/0162505 A1 | 7/2007 | Cecchi et al. |
| 2007/0186165 A1 | 8/2007 | Maislos et al. |
| 2007/0192108 A1 | 8/2007 | Konchitsky |
| 2007/0183604 A1 | 9/2007 | Araki et al. |
| 2007/0208569 A1 | 9/2007 | Subramanian et al. |
| 2007/0265531 A1 | 11/2007 | He et al. |
| 2007/0270659 A1 | 11/2007 | Giegerich |
| 2008/0045805 A1 | 2/2008 | Sarel et al. |
| 2008/0045832 A1 | 2/2008 | McGrath |
| 2008/0074307 A1 | 3/2008 | Boric-Lubecke et al. |
| 2008/0077015 A1 | 3/2008 | Boric-Lubecke et al. |
| 2008/0162352 A1 | 7/2008 | Gizewski |
| 2008/0188752 A1 | 8/2008 | Randall et al. |
| 2008/0208015 A1 | 8/2008 | Morris et al. |
| 2008/0215617 A1 | 9/2008 | Cecchi et al. |
| 2008/0238757 A1 | 10/2008 | Lin et al. |
| 2008/0260212 A1 | 10/2008 | Moskal et al. |
| 2008/0269589 A1 | 10/2008 | Thijs et al. |
| 2008/0300805 A1 | 12/2008 | Li et al. |
| 2008/0302187 A1 | 12/2008 | Huber et al. |
| 2009/0063154 A1 | 3/2009 | Gusikhin et al. |
| 2009/0076343 A1 | 3/2009 | James et al. |
| 2009/0128567 A1 | 5/2009 | Shuster et al. |
| 2009/0156907 A1 | 6/2009 | Jung et al. |
| 2009/0176257 A1 | 7/2009 | Bahn et al. |
| 2009/0203972 A1 | 8/2009 | Heneghan et al. |
| 2009/0216093 A1 | 8/2009 | Sebastian |
| 2009/0292180 A1 | 11/2009 | Mirow |
| 2009/0313019 A1 | 12/2009 | Kato et al. |
| 2010/0083320 A1 | 4/2010 | Roberts et al. |
| 2010/0130873 A1 | 5/2010 | Yuen et al. |
| 2010/0158331 A1 | 6/2010 | Jacobs et al. |
| 2010/0179438 A1 | 7/2010 | Heneghan et al. |
| 2010/0198083 A1 | 8/2010 | Lin et al. |
| 2010/0204587 A1 | 8/2010 | Lin et al. |
| 2010/0205541 A1 | 8/2010 | Rapaport et al. |

(56) References Cited

U.S. PATENT DOCUMENTS

| | | |
|---|---|---|
| 2010/0226504 A1 | 9/2010 | Watanabe |
| 2010/0241009 A1 | 9/2010 | Petkie |
| 2010/0241010 A1 | 9/2010 | Lin et al. |
| 2010/0281986 A1 | 11/2010 | Toal et al. |
| 2011/0060215 A1 | 3/2011 | Tupin et al. |
| 2011/0183305 A1 | 7/2011 | Orbach |
| 2011/0288379 A1 | 11/2011 | Wu |
| 2012/0022348 A1 | 1/2012 | Droitcour et al. |
| 2015/0241555 A1 | 8/2015 | Lin et al. |
| 2016/0336989 A1 | 11/2016 | Lin et al. |

FOREIGN PATENT DOCUMENTS

| | | |
|---|---|---|
| JP | 2006055504 | 3/2006 |
| JP | 2007-010373 | 1/2007 |
| SU | 1337875 | 9/1987 |
| WO | 2004/013611 | 2/2004 |
| WO | 2007/010460 | 1/2007 |
| WO | 2008/151141 | 12/2008 |
| WO | 2009/009690 | 1/2009 |
| WO | 2009/009722 | 1/2009 |
| WO | 2009/076298 | 6/2009 |
| WO | 2010/148141 | 12/2010 |

OTHER PUBLICATIONS

Droitcour, Non-contact measurement of heart and respiration rates with a single-chip microwave Doppler radar, pp. 1-427, Jun. 2006.*

Li, C. et al., "Complex Signal Demodulation and Random Body Movement Cancellation Techniques for Non-Contact Vital Sign Detection", Microwave Symposium Digest, IEEE MTT-S International, Jun. 2008, pp. 567-570.

Park, B. et al., "Arctangent Demodulation with DC Offset Compensation in Quadrature Doppler Radar Receiver Systems", IEEE Trans. Microwave Theory and Techniques, May 2007, pp. 1073-1079, vol. 55, No. 5.

Li, C. et al., "Design Guidelines for Radio Frequency Non-Contact Vital Sign Detection," Proceedings of the 291th Annual International Conference of the IEEE EMBS, Aug. 2007, pp. 1651-1654.

Li, C. et al., "Optimal Carrier Frequency of Non-Contact Vital Sign Detectors," Proceedings of IEEE Radio and Wireless Symposium, Jan. 2007, pp. 281-284.

Droitcour, A.D. et al., "Range Correlation and I/Q Performance Benefits in Single-Chip Silicon Doppler Radars for Non-Contact Cardiopulmonary Monitoring," IEEE Trans. Microwave Theory and Techniques, Mar. 2004,pp. 838-848, vol. 52, No. 3.

Budge, Jr., M.C. et al., "Range Correlation Effects on Phase and Amplitude Noise", Proc. IEEE Southeast Conf., 1993, pp. 5-9.

Droitcour, A.D., "Non-Contact Measurement of Heart and Respiration Rates with a Single Chip Microwave Doppler Radar," Stanford University, Jun. 2006.

Li, C. et al., "Experiment and Spectral Analysis of a Low-Power Ka-Band Heartbeat Detector Measuring From Four Sides of a Human Body,"IEEE Transactions on Microwave Theory and Techniques, Dec. 2006, pp. 4464-4471, vol. 54, No. 12.

Li, C. et al., "Random Body Movement Cancellation in Doppler Radar Vital Sign Detection," IEEE Transactions on Microwave Theory and Techniques, Dec. 2008, pp. 3143-3152, vol. 56, No. 12.

Xiao, Y. et al., "A Ka-Band Low Power Doppler Radar System for Remote Detection of Cardiopulmonary Motion", Proceedings of the 2005 IEEE Engineering in Medicine and Biology 27th Annual Conference, Sep. 2005, pp. 7151-7154.

Samardzija et al., "Applications of MIMO techniques to Sensing Cardiopulmonary Activity", 2005, pp. 1-4.

Xiao, Y., et al., "Accuracy of a Low-Power Ka-Band Non-Contact Heartbeat Detector Measured from Four Sides of a Human Body," Department of Electrical & Computer Engineering, 2006, pp. 1576-1579.

Blum, T.E., et al., "Advances in Laboratory Modeling of Wave Propagation," Optical Engineering, Oct. 24, 2006.

Castellini, P., et al., "Laser Doppler Vibrometry: Development of Advanced Solutions Answering to Technology's Needs," Mechanical Systems and Signal Processing, Aug. 2006, vol. 20, No. 6, pp. 1265-1285.

Ivanov, E.N., et al., "Microwave Interferometry: Application to Precision Measurements and Noise Reductions Techniques," IEEE Transactions on Ultrasonics, Ferroelectrics, and Frequency Control, Nov. 1998, vol. 45, No. 6, p. 1526-1536.

Kim, S., et al., "On the Development of a Multifunction Millimeter-Wave Sensor for Displacement Sensing and Low-Velocity Measurement," IEEE Transactions on Microwave Theory and Techniques, Nov. 2004, vol. 52, No. 11, pp. 503-2512.

Lai, S.H.Y., "Engine System Diagnosis Using Vibration Data," Computers and Industrial Engineering, Sep. 1993, vol. 25, No. 1-4, pp. 135-138.

Li, C., et al., "Non-Contact Measurement of Periodic Movements by a 22-40GHz Radar Sensor Using Nonlinear Phase Modulation," IEEE/MTT-S International Microwave Symposium, Honolulu, HI, Jun. 2007, pp. 579-582.

MacPherson, W.N., et al., "Multipoint Laser Vibrometer for Modal Analysis," Applied Optics, Jun. 2007, vol. 46, No. 16, pp. 3126-3132.

Stelzer, A., et al., "A Microwave Position Sensor with Sub-Millimeter Accuracy," IEEE Transactions on Microwave Theory and Techniques, Dec. 1999, vol. 47, No. 12, pp. 2621-2624.

Yan, Y., et al., "Effects of I/Q Mismatch on Measurement of Periodic Movement Using a Doppler Radar Sensor," IEEE Radio and Wireless Symposium, 2010, pp. 196-199.

Yan, Y., et al., "Ka-band Quadrature Doppler Radar System with Sub-millimeter Resolution and Sensitivity in Measuring Periodic Movement," 11 1th Annual IEEE Wireless and Microwave Technology Conference, Apr. 2010, pp. 12-13.

Yan, Y., et al., "Wavelength Division Sensing RF Vibrometer," IEEE/MTT-S International Microwave Symposium, Baltimore, MD, Jun. 2011.

Yoshizumi, N., et al., "Multiple-Frequency Ultrasonic Imaging by Transmitting Pulsed Waves of Two Frequencies," Journal of Medical Ultrasonics, Jun. 2009, vol. 36, No. 2, pp. 53-60.

Yan, Y., et al.; Analysis of Detection Methods of RF Vibrometer for Complex Motion Measurement; IEEE Transactions on Microwave Theory and Techniques, vol. 59, No. 12, Dec. 2011; p. 3556-3566.

Cao, Y., et al., "Frequency-Independent Equivalent-Circuit Model for On-Chip Spiral Inductors," IEEE Journal of Solid-State Circuits, Mar. 2003, vol. 38, No. 3, pp. 419-426.

Gao, C., et al., "Millimeter-Wave Voltage-Controlled Oscillators in 0.13-pm CMOS Technology," IEEE Journal of Solid-State Circuits, Jun. 2006, vol. 41, No. 6, pp. 1297-1304.

Chuang, H.R., et al., "60-GHz Millimeter-Wave Life Detection System (MLDS) for Noncontact Human Vital-Sign Monitoring," IEEE Sensors Journal, Mar. 2012, vol. 12, No. 3, pp. 602-609.

Dickson, T.O., et al., "30-100-GHz Inductors and Transformers for Millimeter-Wave (Bi)CMOS Integrated Circuits," IEEE Transactions on Microwave Theory and Techniques, Jan. 2005, vol. 53, No. 1, pp. 123-133.

Jentzsch, A., et al., "Theory and Measurements of Flip-Chip Interconnects for Frequencies up to 100 GHz," IEEE Transactions on Microwave Theory and Techniques, May 2001, vol. 49, No. 5, pp. 871-878.

Kao, T.Y., et al., "Design and Analysis of a 60-GHz CMOS Doppler Micro-radar Systemin-Package for Vital Sign and Vibration Detection," IEEE Transactions on Microwave Theory and Techniques, Mar. 2013, vol. 61, No. 4, pp. 1649-1659.

Kao, T.Y., et al., "A Flip-Chip-Packaged and Fully Integrated 60 GHz CMOS Micro-Radar Sensor for Heartbeat and Mechanical Vibration Detections," IEEE Radio Frequency Integrated Circuits Symposium, Jun. 2012, pp. 443-446.

Kraemer, M., et al., "Accurate Electromagnetic Simulation and Measurement of Millimeter-wave Inductors in Bulk CMOS Technology," Proceedings of the 1dh Topical Meeting on Silicon Monolithic Integrated Circuits in RF Systems, Jan. 2010, pp. 61-64.

Kuo, J.L., et al., "A 50 to 70 GHz Power Amplifier Using 90 nm CMOS Technology," IEEE Microwave and Wireless Components Letters, Jan. 2009, vol. 19, No. 1, pp. 45-47.

(56) References Cited

OTHER PUBLICATIONS

Laskin, E., et al., "Nanoscale CMOS Transceiver Design in the 90-170-GHz Range," IEEE Transactions on Microwave Theory and Techniques, Dec. 2009, vol. 57, No. 12, pp. 3477-3490.
Lee, J., et al., "A Low-Power Low-Cost Fully-Integrated 60-GHz Transceiver System With OOK Modulation and On-Board Antenna Assembly," IEEE Journal of Solid-State Circuits, Feb. 2010, vol. 45, No. 2, pp. 264-275.
Li, C., et al., "High-Sensitivity Software-Configurable 5.8 GHz Radar Sensor Receiver Chip in 0.13 µm CMOS for Non contact Vital Sign Detection," IEEE Transactions on Microwave Theory and Techniques, May 2010, vol. 58, No. 5, pp. 1410-1419.
Liang, C.K., et al., "Systematic Transistor and Inductor Modeling for Millimeter-Wave Design," IEEE Journal of Solid-State Circuits, Feb. 2009, vol. 44, No. 2, pp. 450-457.
Lu, H. C., et al., "Flip-Chip-Assembled W-Band CMOS Chip Modules on Ceramic Integrated Passive Device With Transition Compensation for Millimeter-Wave System-in-Package Integration," IEEE Transactions on Microwave Theory and Techniques, Mar. 2012, vol. 60, No. 3, pp. 766-777.
Pellerano, S., et al., "A 64 GHz LNA With 15.5 dB Gain and 6.5 dB NF in 90 nm CMOS," IEEE Journal of Solid-State Circuits, Jul. 2008, vol. 43, No. 7, pp. 1542-1552.
Petkie, D.T., et al., "Millimeter Wave Radar for Remote Measurement of Vital Signs," IEEE Radar Conference, May 2009, pp. 1-3.
Reynolds, S.K., et al., "A Silicon 60-GHz Receiver and Transmitter Chipset for Broadband Communications," IEEE Journal of Solid-State Circuits, Dec. 2006, vol. 41, No. 12, pp. 2820-2831.
Yan, W.S.T., et al., "A 900-MHz CMOS Low-Phase-Noise Voltage-Controlled Ring Oscillator," IEEE Transactions on Circuits and Systems II: Analog and Digital Signal Processing, Feb. 2001, vol. 48, No. 2, pp. 216-221.
Yao, T., et al., "Algorithmic Design of CMOS LNAs and PAs for 60-GHz Radio," IEEE Journal of Solid-State Circuits, May 2007, vol. 42, No. 5, pp. 1044-1057.
Benotsch, E.G., et al. "Rapid Anxiety Assessment in Medical Patients: Evidence for the Validity of Verbal Anxiety Readings," Annals of Behavioral Medicine, 2000, vol. 22, No. 3, pp. 199-203.
Camacho, A., "Swipe: A Sawtooth Waveform Inspired Pitch Estimator for Speech and Music," Doctoral dissertation, University of Florida, 2007.
Froming, K.B., et al., "Comprehensive Affect Testing System (CATS)", 2006, http://www.psychologysoftware.com/CATS.htm.
Geisheimer, J., et al., "A Non-Contact Lie Detector Using Radar Vital Signs Monitor (RVSM) Technology," IEEE Aerospace and Electronic Systems Magazine, Aug. 2001, vol. 16, No. 8, pp. 10-14.
Gobl, C., et al., "The Role of Voice Quality in Communicating Emotion, Mood and Attitude," Speech Communication, Apr. 2003, vol. 40, Nos. 1-2, pp. 189-212.
Hillenbrand, J., et al., "Acoustic Correlates of Breathy Vocal Quality: Dysphonic Voices and Continuous Speech," Journal of Speech and Hearing Research, Apr. 1, 1996, vol. 39, No. 2, pp. 311-321.
Patel, S., "Acoustic Correlates of Emotions Perceived from Suprasegmental Cues in Speech," Doctoral dissertation, University of Florida, 2009.
Scherer, K.R., "Vocal Affect Expression: A Review and a Model for Future Research," Psychological Bulletin, Mar. 1986, vol. 99, No. 2, pp. 143-165.
Schroder, M., "Experimental Study of Affect Bursts," Speech Communication, Apr. 2003, vol. 40, Nos. 1-2, pp. 99-116.
Venkatesh, S., et al., "Implementation and Analysis of Respiration-Rate Estimation Using Impulse-Based UWB," IEEE Military Communications Conference, Oct. 17-20, 2005, vol. 5, pp. 3314-3320.
Westbrook, R.A., et al., "The Dimensionality of Consumption Emotion Patterns and Consumer Satisfaction," Journal of Consumer Research, Jun. 1991, vol. 18, No. 1, pp. 84-91.
Xiao, Y., et al., "A Portable Noncontact Heartbeat and Respiration Monitoring System Using 5-GHz Radar", IEEE Sensors Journal, pp. 1042-1043, Jul. 2007, vol. 7, No. 7.
Li, C., et al., "Robust Overnight Monitoring of Human Vital Signs by a Non-Contact Respiration and Heartbeat Detector", 28th IEEE EMBS Annual International Conf., pp. 2235-2238, 2006.
Xiao, Y., et al., "Frequency-Tuning Technique for Remote Detection of Heartbeat and Respiration Using Low-Power Double-Sideband Transmission in the Ka-Band", IEEE Trans. on Microwave Theory and Techniques, pp. 2023-2032, May 2006, vol. 54, No. 5.
Chen, K., et al., "Microwave Life Detection Systems for Searching Human Subjects Under Earthquake Rubble or Behind Barrier", IEEE Trans. on Biomedical Eng., p. 105-114, Jan. 2000, vol. 27, No. 1.
Abramov et al., English Abstract RU 2295911, Mar. 2007.
Lin, "Microwave Doppler Radar Sensor for Detection of Human Vital Signs and Mechanical Vibrations", Feb. 10, 2012. [retrieved on Nov. 19, 2015]. Retrieved from the Internet. <URL: http:I/abe.ufl.edu/research/CRS/seminar/20120210_Lin_Seminar.pdf>.
Pan et al., "A real-time QRS detection algorithm," IEEE Trans. Biomed. Eng., Mar. 1985, vol. 32, No. 3, pp. 230-236.
Razavi, B., "Design Considerations for Direct-Conversion Receivers," IEEE Trans. on Circuits and Systems II: Analog and Digital Signal Processing, Jun. 1997, vol. 44, No. 6, pp. 428-435.
Gu et al., "Instrument-based noncontact Doppler radar vital sign detection system using heterodyne digital quadrature demodulation architecture," IEEE Trans. Instrum. Meas., Jun. 2010, vol. 59, No. 6, pp. 1580-1588.
Lin, James C. "Noninvasive microwave measurement of respiration." Proceedings of the IEEE 63.10 (Oct. 1975): 1530-1530.
Yavari, Ehsan, and Olga Boric-Lubecke. "Low IF demodulation for physiological pulse Doppler radar." Microwave Symposium (IMS), 2014 IEEE MTT-S International. IEEE, (Jun. 2014).
Gu, Changzhan, et al. "Instrument-based noncontact Doppler radar vital sign detection system using heterodyne digital quadrature demodulation architecture." IEEE Transactions on Instrumentation and Measurement 59.6 (Jun. 2010): 1580-1588.
Mostafanezhad, Isar, and Olga Boric-Lubecke. "Benefits of coherent low-IF for vital signs monitoring using Doppler radar." IEEE Transactions on Microwave Theory and Techniques 62.10 (Oct. 2014): 2481-2487.
Ramachandran, G., and M. Singh. "Three-dimensional reconstruction of cardiac displacement patterns on the chest wall during the P, QRS and T-segments of the ECG by laser speckle inteferometry." Medical and Biological Engineering and Computing 27.5 (Sep. 1989): 525-530.
Singh, Megha, and G. Ramachandran. "Reconstruction of sequential cardiac in-plane displacement patterns on the chest wall by laser speckle interferometry." IEEE transactions on biomedical engineering 38.5 (May 1991): 483-489.

\* cited by examiner

RANDOM BODY MOVEMENT CANCELLATION FOR NON-CONTACT VITAL SIGN DETECTION

CROSS REFERENCE TO RELATED APPLICATIONS

The present application is a continuation of co-pending U.S. application Ser. No. 14/276,300, filed May 13, 2014, which is a continuation of U.S. application Ser. No. 12/668,700, filed Jan. 12, 2010, which is the U.S. national stage application of International Application No. PCT/US2008/069766, filed Jul. 11, 2008, which claims the benefit of U.S. Provisional Application Ser. No. 60/949,285, filed Jul. 12, 2007, each of which is hereby incorporated by reference herein in its entirety, including any figures, tables, nucleic acid sequences, amino acid sequences, or drawings.

FIELD OF THE INVENTION

The present invention relates generally to non-contact monitoring and more specifically a method and system to eliminate random body movements during non-contact vital sign monitoring.

BACKGROUND OF THE INVENTION

In practical applications of non-contact vital sign detection, the noise caused by irregular body movement presents severe interference for accurate detection of vital signs such as respiration and heartbeat signal. Since random body movement is comparable or even stronger than the weak vital sign signal, to some extent it is the main factor limiting the applications of non-contact vital sign sensors.

To reduce body movement, prior art techniques require that the subject or patient being monitored remain stationary and motionless. In many applications such as healthcare, sports, law enforcement, security, it is difficult if not impossible to have the subject being monitored to remain stationary.

Accordingly, what is needed is a method and a system to overcome the aforementioned problems and to recover severely distorted signals during non-contact vital sign detection even when the subject is not stationary.

SUMMARY OF THE INVENTION

The present invention provides a method and a system to cancel out noise due to random body movement during non-contact vital sign monitoring. The present invention recovers severely distorted signal to obtain accurate measurement result, solving the main problem prohibiting the wide daily application of non-contact vital sensors.

Described is a random body movement cancellation in quadrature Doppler radar non-contact vital sign detection using complex signal demodulation and the arctangent demodulation. Applications using the present invention include sleep apnea monitor, lie detector, and baby monitor to eliminate the false alarm caused by random body movement. It has been shown that if the DC offset of the baseband signal is accurately calibrated, both demodulation techniques can be used for random body movement cancellation. While the complex signal demodulation is less likely to be affected by a DC offset, the arctangent demodulation has the advantage of eliminating harmonic and intermodulation interference at high carrier frequencies. In applications where the DC offset cannot be accurately calibrated, the complex signal demodulation is used. Ray-tracing model is used to show the effects of constellation deformation and optimum/null detection ambiguity caused by the phase offset due to finite antenna directivity. Experiments have been performed using 4-7 GHz radar.

In one embodiment the present invention method for cancelling random body by sending at least two electromagnetic signals comprising a first electromagnetic signal with a first frequency to a first side of a body from a first electromagnetic wave transceiver and a second electromagnetic signal with a second frequency to a second side of a body from a second electromagnetic wave transceiver. A first reflected electromagnetic signal reflected back in response to the first electromagnetic wave on the first transceiver is received and a first baseband complex signal is extracted. Likewise a second reflected electromagnetic signal reflected back in response to the second electromagnetic wave on the second transceiver is received and a second baseband complex signal is extracted. The first baseband complex signal is mathematically combined with the second baseband complex signal to cancel out a Doppler frequency drift therebetween to yield a periodic Doppler phase effect. Vital signs such as respiration rate and heart rate are extracted from the signal representing the periodic Doppler phase effect.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention will be apparent from the following detailed description taken in conjunction with the accompanying drawings in which:

(FIG. 2A) a complex signal demodulation; and (FIG. 2B) an arctangent demodulation, according to the present invention.

(FIG. 3A) ray-tracing model and the angular information (FIG. 3B) ray-tracing model of signals reflected from point A and B on the body using a 5.8 GHz radar, according to the present invention.

(FIG. 4A) the phase offset on the surface of human body radiated by a 5.8 GHz radar; (FIG. 4B) a 7 by 7 elements antenna array's radiation intensity on the human body; (FIG. 4C) approximation of the normalized amplitude of body movement caused by respiration; and (FIG. 4D) approximation of the normalized amplitude of body movement caused by heartbeat, according to the present invention.

(FIG. 5A) a signal detected at heart center (Case I) and at body center (Case II); (FIG. 5B) an actual received signal (Case III); (FIG. 5C) an angular information $\psi(t)$ of the received signal; and (FIG. 5D) baseband spectra obtained by the complex signal demodulation and the arctangent demodulation (the DC component is not shown in the baseband spectrum).

(FIG. 6A) a signal detected at heart center (Case I) and at body center (Case II); (FIG. 6B) an actual received signal (Case III), with the recovered angular information shown in inset; (FIG. 6C) a baseband spectra obtained by the complex signal demodulation and the arctangent demodulation (DC component not shown in the spectra), according to the present invention.

(FIG. 7A) a spectrum of a single-beam signal projected to the heart center; and (FIG. 7B) a spectrum of the actually received signal, according to the present invention.

(FIG. 8A) the random body movement is shown in the Z, X, and Y directions, which are defined in FIGS. 3A-3B; and (FIG. 8B) a baseband spectra by arctangent demodulation (AD) and complex signal demodulation (CSD), according to the present invention.

(FIG. 9A) angular information and baseband spectrum; and (FIG. 9B) angular information recovered by random body movement cancellation (RBMC) using the two demodulation techniques; accurate DC information is used in demodulation but not shown in the spectrum, according to the present invention.

(FIG. 10A) angular information and baseband spectrum; and (FIG. 10B) angular information recovered from the random body movement cancellation (RBMC) technique; the random body movements are modeled in three dimensions, and the DC offset in each transceiver is 30% of the maximum signal amplitude, according to the present invention.

(FIG. 12A) a trajectory of detected baseband signal with no DC information and with estimated DC offset level added; and (FIG. 12B) a spectra obtained by the two demodulation techniques. Signal with estimated DC offset added was used for arctangent demodulation.

FIGS. 13A-13B show a graph of signals detected from: (FIG. 13A) the front of a human body; and (FIG. 13B) the back of the human body, according to the present invention.

(FIG. 14A) a spectra measured from the front and the back of the human body; (FIG. 14B) a spectrum from combining the two transceiver outputs, the heartbeat information cannot be recovered due to inaccurate DC offset information, according to the present invention.

(FIG. 15A) a spectra measured from the front and the back of the human body; and (FIG. 15B) an output spectrum by the random body movement cancellation technique, the heartbeat information is recovered, according to the present invention.

DESCRIPTION OF THE PREFERRED EMBODIMENTS

Figure 1:
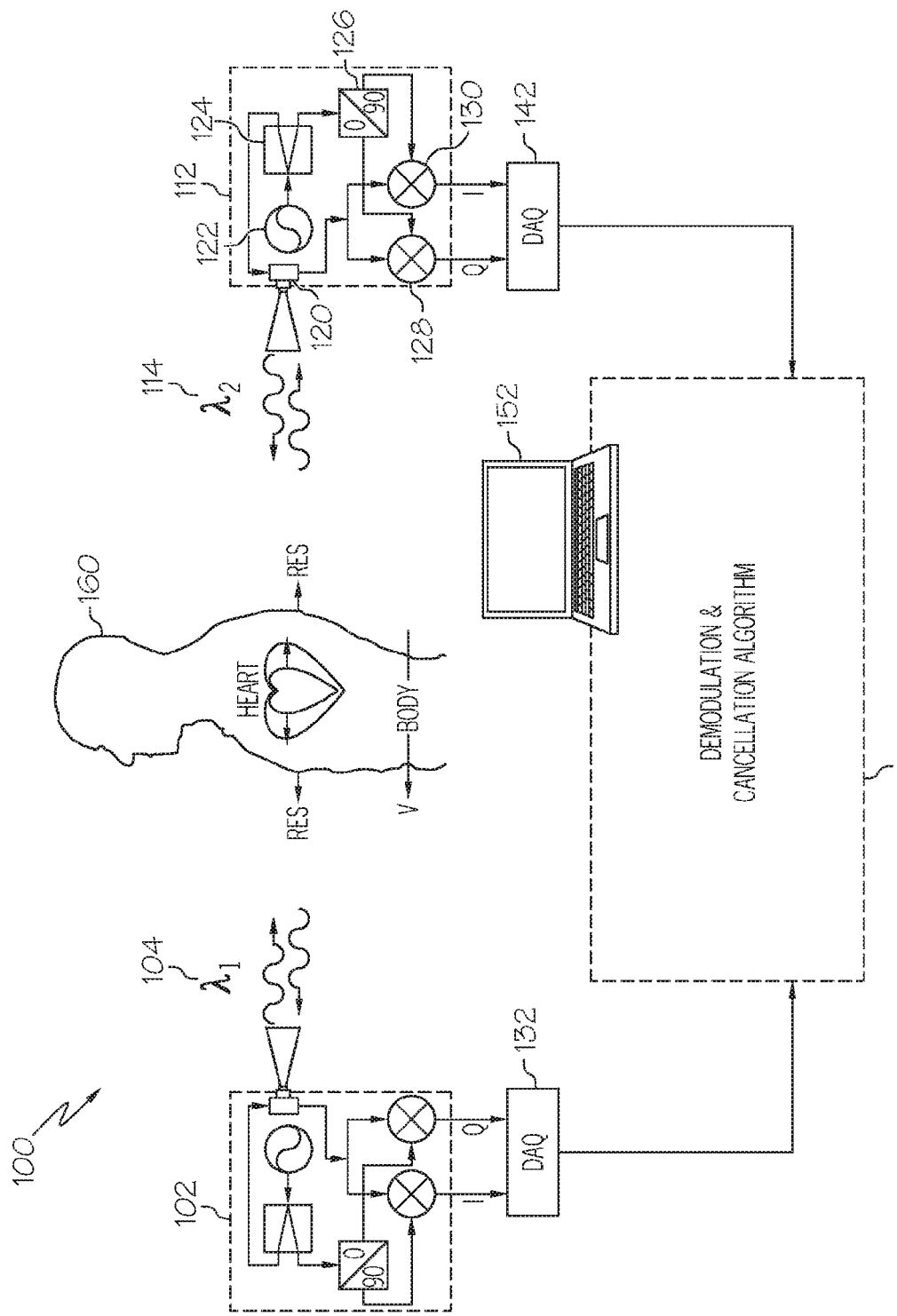
FIG. 1 is a system diagram of the multi-antenna and multi-wavelength technique, according to the present invention.

It should be understood that these embodiments are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality. The term "body" or "patient" or "person" or "subject" is used interchangeably herein to refer to any living organism that has vital signs such as heart beat and respiration including humans and animals.

I. INTRODUCTION

The present invention has many advantages over the prior art system. One advantage is the present invention cancels out noise due to random body movement during non-contact vital sign monitoring. The present invention recovers severely distorted signal to obtain accurate measurement result, solving the main problem prohibiting the wide daily application of non-contact vital sensors.

Further, the present invention does not require subjects to remain stationary and motionless. It makes the existing applications of non-contact sensing more robust. This has broad application in such diverse areas as healthcare, sports, law enforcement, security, social networking where the subjects may move around during detection. Improved applications include monitoring systems, biomedical sensors, lie detectors, military personal radar carried by soldiers for behind-the-wall sensing, and security systems. All of the above systems and applications are non-contact and can be made portable.

In one embodiment the present invention uses a complex signal demodulation used for random body movement cancellation. In another embodiment of the present invention uses an important demodulation method of non-contact vital sign detection, i.e. the arctangent demodulation, for random body movement cancellation. It is shown that if the baseband DC offset information is known, both of the two demodulation techniques can be used for random body movement cancellation. When the DC offset cannot be accurately calibrated out, the complex signal demodulation is more favorable for random body movement cancellation. The ray-tracing model used illustrates the effects of constellation deformation and optimum/null detection ambiguity caused by the phase offset due to finite antenna directivity.

Two modulations embodiments are described in order to mathematically combine the first baseband complex signal with the second baseband complex signal to cancel out a Doppler frequency drift in order to yield a periodic Doppler phase effect. The two demodulation embodiments and their implementation for random body movement cancellation are described below in the section entitled II Complex-Signal Demodulation and Arctangent Demodulation. The effect of phase offset is discussed in Section III. Simulations have been performed and the results are reported in Section IV. Experimental results are presented in Section V, and a conclusion is drawn in Section VI.

II. COMPLEX-SIGNAL DEMODULATION AND ARCTANGENT DEMODULATION

The present invention utilizes a multi-antenna and multi-wavelength technique that combines signals detected from different body orientation to cancel out random body movements based on different Doppler frequency shifts detected. This technique can recover severely distorted signal to achieve robust non-contact measurement of heartbeat rate and respiration rate from a distance away. This invention includes the theory/method and both the hardware system and software algorithm to implement the method. When random body movement is present and it affects accurate detection, the measurement has to be performed simultaneously from both sides to cancel out the random frequency drift. This is described further in the publication by C. Li, and J. Lin, "Complex Signal Demodulation and Random Body Movement Cancellation Techniques for Non-contact Vital Sign Detection," IEEE MTT-S International Microwave Symposium Digest, June, 2008, which is hereby incorporate by reference in its entirety.

Turning now to FIG. 1, shown is a system diagram 100 or Doppler radar non-contact vital sign detection. The system 100 includes the multi-transceiver 102, 112 and multi-wavelength technique 104 and 114 i.e. $\lambda$ and $\lambda$. The two transceivers, one in front of and the other behind the subject 160, are transmitting and receiving signals with different wavelength to avoid interference to each other. It is important to note that although the transceivers are shown in front and back, other positions such as one side of the body and the other side of the body can be used.

In one embodiment, each transceiver 102 and 112 is identical. A signal generator 122 is fed into a splitter 124. One output of the splitter is fed to a quadrature splitter 126 and the other output fed to the transmitter output through a circulator 120 producing wave $\lambda$ 114. The signal received which is reflected off the subject 160 through circulator 120 is fed to multipliers 128 and 130 followed by a quadrature splitter 126 to produce an output. The output quadrature Q and in-phase I component of each down sampled signal from each transceiver 102 and 112 are directed to a respective DAQ (digital acquisition module) 132, 142. Each DAQ 132 and 142 is fed to a movement cancellation algorithm 150. In one embodiment the body movement cancellation algorithm 150 is implemented as part of a computer. More specifically the body movement cancellation algorithm 150 is implemented in software to process the signals detected from different transceivers. The resulting detected wave is outputted to a display 152 or other output device such as a printer, buzzer, or wireless to a remote monitoring station (not shown). This algorithm is described further in the sections below. It is important to note that the present invention can be implemented in a combination of hardware and software, such as dedicated hardware system and that the present invention is not limited to using a computer to implement this algorithm.

In the analysis of non-contact quadrature demodulation of vital sign, the single-beam model assumes an ideal antenna with infinite directivity focusing a beam at the location of the heart. When no random body movement is present, the normalized detected baseband signal in one of the baseband I/Q channels can be represented and analyzed by spectral analysis:

$$B(t) = \cos\left(\frac{4\pi x_h(t)}{\lambda} + \frac{4\pi x_r(t)}{\lambda} + \phi\right) \quad (1)$$

$$= \sum_{k=-\infty}^{\infty} \sum_{l=-\infty}^{\infty} J_l\left(\frac{4\pi m_h}{\lambda}\right) J_k\left(\frac{4\pi m_r}{\lambda}\right) \cos(k\omega_r t + l\omega_h t + \phi)$$

where $x_h(t) = m_h \cdot \sin \omega_h t$, $x_r(t) = m_r \cdot \sin \omega_r t$ are the periodic body movements due to heartbeat and respiration, $\lambda$ is the wavelength of the wireless signal, $\phi$ is the total residual phase accumulated in the circuit and along the transmission path, and Jn is the Bessel function of the first kind.

For a quadrature transceiver, the baseband output in the I/Q channel can be represented as B(t) and the quadrature of B(t). Meanwhile, the Bessel coefficient with a negative index number and a positive index number in equation (1) can be combined using the property: $Jn(x)=J-n(x)$ for even numbers of n and $Jn(x)=-J-n(x)$ for odd numbers of n. Therefore, the baseband I/Q output can be represented as:

$$I(t) = \cos\left(\frac{4\pi x_h(t)}{\lambda} + \frac{4\pi x_r(t)}{\lambda} + \phi\right) \quad (2.a)$$
$$= DC_I - 2[C_{10}\sin(\omega_r t) + C_{01}\sin(\omega_h t) + \ldots] \cdot \sin\phi +$$
$$2[C_{20}\cos(2\omega_r t) + C_{02}\cos(2\omega_h t) + \ldots] \cdot \cos\phi$$

$$Q(t) = \sin\left(\frac{4\pi x_h(t)}{\lambda} + \frac{4\pi x_r(t)}{\lambda} + \phi\right) \quad (2.b)$$
$$= DC_Q + 2[C_{10}\sin(\omega_r t) + C_{01}\sin(\omega_h t) + \ldots] \cdot \cos\phi +$$
$$2[C_{20}\cos(2\omega_r t) + C_{02}\cos(2\omega_h t') + \ldots] \cdot \sin\phi$$

where $Cij = Ji(4\pi mr/\lambda) \cdot Jj(4\pi mh/\lambda)$ determines the amplitude of every frequency component. The ellipses in equations (2.a) and (2.b) represent higher order odd and even harmonics.

From equations (2.a) and (2.b), the ratio of cos $\phi$ and sin $\phi$ determines the relative strength between the even order and the odd order harmonics. Therefore, the optimal/null detection point is determined by the residue phase $\phi$. For example, when $\phi$ is close to 90°, the fundamental frequency of respiration and heartbeat signals dominates in the I channel while the second order harmonic of desired signals dominates in the Q channel, thus I is close to the optimal detection point and Q is close to the null detection point. According to the single-beam model, when either one of the two quadrature channels is close to an optimal detection point, the other one should be close to the null detection point.

A. Complex Signal Demodulation

It is important to note that although the frequency of wavelengths $\lambda$ and $\lambda$ are described as substantially similar, these frequencies can be selected to be very close to each other. The lack of a phase-lock loop coupled between transceivers 102 and 112 is the cause for this slight difference.

Two free running VCOs are used for the two transmitters so that $\lambda_1$ and $\lambda_2$ are close to each other but always have a slight difference because the system does not incorporate any phase-locked-loop. This provides the following advantages: Firstly, the signal from one transceiver can be easily rejected by the other transceiver, because the slight difference in radio frequency results in a large difference in baseband signal for vital sign detection and can easily filter out signal from the other transceiver. Secondly, since $\lambda_1$ and $\lambda_2$ are set very close, it enables the movement cancellation method to cancel out Doppler frequency shift due to random body movement, as will be shown theoretically in the following. Finally, the free running VCO without phase-locked-loop significantly reduces the complexity and cost of this technique.

Figure 2A:
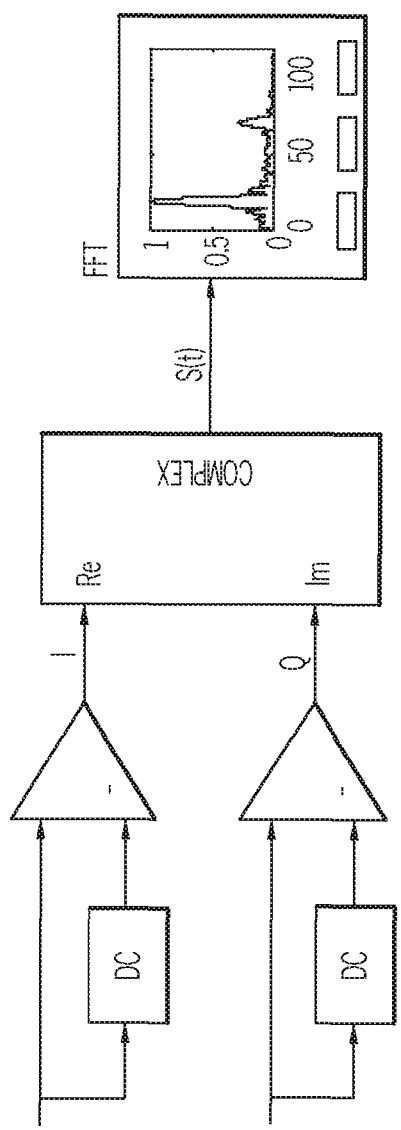
FIGS. 2A-2B show block diagrams illustrating.
Figure 2B:
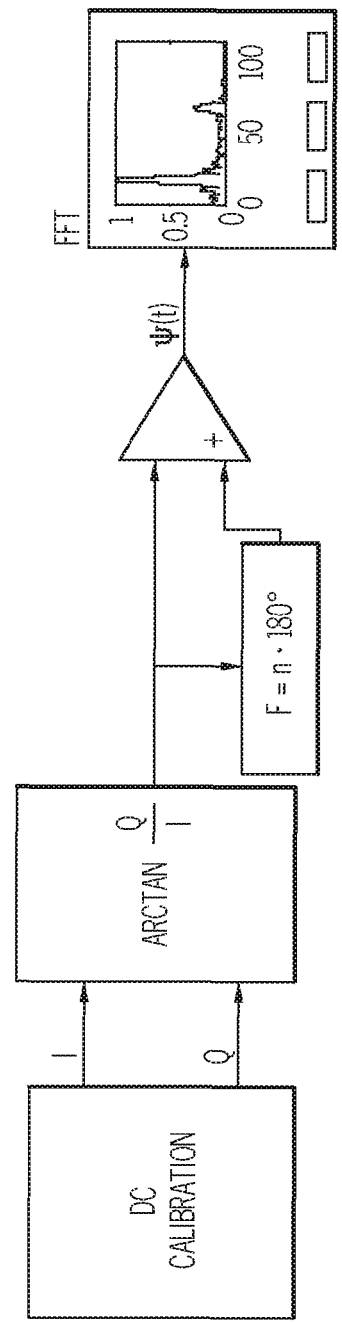

Referring now to FIGS. 2A-2B shown is a block diagram illustrating: (FIG. 2A) a complex signal demodulation; and (FIG. 2B) an arctangent demodulation, according to the present invention. The complex signal demodulation of FIG.

2A can eliminate the optimum/null detection point problem by combining the I and Q signals in baseband. As shown in Equation (2.a), the complex signal is softward-reconstructed in real time as:

$$S(t) = I(t) + j \cdot Q(t) \quad (3)$$
$$= \exp\left\{ j\left[\frac{4\pi x_h(t)}{\lambda} + \frac{4\pi x_r(t)}{\lambda} + \phi\right]\right\}$$
$$= DC_{IQ} + 2j[C_{10}\sin(\omega_r t) + C_{01}\sin(\omega_h t) + \ldots ] \cdot e^{j\phi} +$$
$$2[C_{20}\cos(2\omega_r t) + C_{02}\cos(2\omega_h t) + \ldots ] \cdot e^{j\phi}$$

where $e^{j\phi}$ has a constant envelope of one, and thus the effect of $\phi$ on signal amplitude can be eliminated. Applying the complex Fourier transform to the signal S(t) for spectral analysis, the residual phase $\phi$ will not affect the relative strength between the odd order and the even order frequency components. The desired signal components (odd order tones) will always be present in the spectrum.

Meanwhile, the DC components accumulated in the I and the Q channels only contribute to the DC term in the complex signal S(t), thus does not affect obtaining the frequency of the desired signal component. In practice, the residual baseband DC components can be easily extracted as the average of signals in every time-domain sliding window and thus be safely removed. As a result, the complex signal demodulation greatly simplifies the demodulation procedure and is immune from DC offset when no random body movement is present. However, the complex signal demodulation is not able to completely eliminate the higher even order harmonics.

For random body movement cancellation, measurements need to be performed from both sides of the human body. In this way, the signal detected from the two transceivers can be expressed as:

$$S_f(t) = \exp\left\{ j\left[\frac{4\pi x_{h1}(t)}{\lambda} + \frac{4\pi x_{r1}(t)}{\lambda} + \frac{4\pi y(t)}{\lambda} + \phi_1\right]\right\} \quad (4.a)$$

$$S_b(t) = \exp\left\{ j\left[\frac{4\pi x_{h2}(t)}{\lambda} + \frac{4\pi x_{r2}(t)}{\lambda} - \frac{4\pi y(t)}{\lambda} + \phi_2\right]\right\} \quad (4.b)$$

where $x_{h1}(t)$ and $x_{r1}(t)$ are the heartbeat-induced and the respiration-induced physiological movements on the front chest wall, $x_{h2}(t)$ and $x_{r2}(t)$ are the heartbeat-induced and the respiration-induced physiological movements on the back, $\phi_1$, $\phi_2$ are the residual phase of the transceivers in front of the body and behind the body, and y(t) is the random body movement. Note that the pairs of physiological movements on both sides of the body, e.g. $x_{h1}(t)$ and $x_{h2}(t)$, move in the same direction relative to their respective detecting radar. On the other hand, when the body is drifting toward one of the radars, it is moving away from the other one. Therefore, by multiplying $S_f(t)$ and $S_b(t)$, the y(t) term in the baseband output $S_{fb}(t)=S_f(t) \cdot S_b(t)$ will be cancelled out, while the physiological movement terms are enhanced:

$$S_{fb}(t) = \exp\left\{ j\left[\frac{4\pi[x_{h1}(t) + x_{h2}(t)]}{\lambda} + \frac{4\pi[x_{r1}(t) + x_{r2}(t)]}{\lambda} + \phi_1 + \phi_2\right]\right\} \quad (5)$$

The above operation can also be interpreted as convolution and frequency shift in frequency domain, thus canceling the Doppler frequency drift and keeping only the periodic Doppler phase effects.

Although it is shown that the complex signal demodulation itself does not require the baseband DC offset information, the performance of random body movement cancellation is affected by the DC offset. Proper estimation or calibration of the DC offset is beneficial for successful cancellation of the noise due to random body movement.

B. Arctangent Demodulation

Referring now to FIG. 2B shown is block diagram of arctangent demodulation, according to the present invention. Another way to eliminate the optimum/null detection point problem in the quadrature demodulation system is to use arctangent demodulation by calculating the total Doppler phase shift. Its block diagram is shown in FIG. 2B. This is described further in the publication by B. Park, O. Boric-Lubecke, and V. M. Lubecke, "Arctangent demodulation with DC offset compensation in quadrature Doppler radar receiver systems", IEEE Trans. Microwave Theory and Techniques, vol. 55, pp. 1073-1079, May 2007, which is hereby incorporate by reference in its entirety. Taking into account the phase discontinuity when the signal trajectory crosses the boundary of two adjacent quadrants, the arctangent demodulation calculates the total angular information $\psi(t)$ as:

$$\psi(t) = \arctan\frac{Q(t)}{I(t)} + F = \frac{4\pi x_h(t)}{\lambda} + \frac{4\pi x_r(t)}{\lambda} + \phi \quad (6)$$

where F is a multiple of 180° for the purpose of eliminating the discontinuity when $\psi(t)$ crosses the boundary of two adjacent quadrants in the constellation graph.

Because $\psi(t)$ is a linear combination of the desired signal $x_h(t)$ and $x_r(t)$, the information of the vital signs can be obtained with the nonlinear phase modulation effect eliminated. The advantage is the ability to eliminate the harmonic and intermodulation interference. However, previous demonstration of this embodiment accurate calibration of the DC offset is needed in order to properly reconstruct the angular information. This is described further in the publication by B. Park, O. Boric-Lubecke, and V. M. Lubecke, "Arctangent demodulation with DC offset compensation in quadrature Doppler radar receiver systems", IEEE Trans. Microwave Theory and Techniques, vol. 55, pp. 1073-1079, May 2007, which is hereby incorporate by reference in its entirety.

The difficulty of accurate DC offset calibration encountered in Doppler radar vital sign detection is that the DC offset is not only produced by the electronic circuit, but also by the unmodulated reflected signal, i.e. signal reflected from stationary objects and other parts of the human body rather than the moving chest wall. Therefore, the DC offset changes as the environment changes and needs to be calibrated when it is changed. Again, this is described further in the publication by B. Park, O. Boric-Lubecke, and V. M. Lubecke, "Arctangent demodulation with DC offset compensation in quadrature Doppler radar receiver systems", IEEE Trans. Microwave Theory and Techniques, vol. 55, pp. 1073-1079, May 2007, which is hereby incorporate by reference in its entirety.

On the other hand, the presence of baseband DC offset results in a shifted trajectory in the constellation graph. Although the angular information $\psi(t)$ will be changed significantly when the trajectory is shifted, the angular movement is still periodic. This implies that when analyzing the spectrum of $\psi(t)$ in the presence of a DC offset, the desired frequency components still exist. The difference observed in the spectrum is a changed harmonic level. Therefore, if the DC offset can be properly estimated, it is still possible to extract the desired vital signs. As will be demonstrated in Section V, a trajectory-fitting procedure is adopted in this paper for DC offset estimation in baseband. Experiments will show that this procedure can be used for vital sign detection in the absence of random body movement.

When random body movement is present, the angular information recovered from the front ($\psi_f$) and the back ($\psi_b$) of the human body can be expressed as:

$$\psi_f(t) = \frac{4\pi x_{h1}(t)}{\lambda} + \frac{4\pi x_{r1}(t)}{\lambda} + \frac{4\pi y(t)}{\lambda} + \phi_1 \quad (7.a)$$

$$\psi_b(t) = \frac{4\pi x_{h2}(t)}{\lambda} + \frac{4\pi x_{r2}(t)}{\lambda} - \frac{4\pi y(t)}{\lambda} + \phi_2 \quad (7.b)$$

where $x_{h1}(t)$, $x_{r1}(t)$, $x_{h2}(t)$, $x_{r2}(t)$, $\phi_1$, and $\phi_2$ are the same as defined in Section II-A. Instead of multiplying the two signals as in the case of using complex signal demodulation, the random body movement can be cancelled out by adding the angular information of equations (7.a) and (7.b) together to obtain $\psi_{fb}(t) = \psi_f(t) + \psi_b(t)$:

$$\psi_{fb}(t) = \frac{4\pi[x_{h1}(t) + x_{h2}(t)]}{\lambda} + \frac{4\pi[x_{r1}(t) + x_{r2}(t)]}{\lambda} + \phi_1 + \phi_2 \quad (8)$$

III. EFFECTS OF PHASE OFFSET

Since a real antenna with a certain radiation pattern does not have infinite directivity, signals are reflected and captured from different parts of the body. When signals on different paths with different intensity and residual phases are received by the radar, they are simply summed together by the receiving antenna, either canceling out or enhancing the desired signal components. Therefore, a ray-tracing model is developed to compensate for the shortage of the single-beam model. This is described further in the publication by C. Li, Y. Xiao, and J. Lin, "Design Guidelines for Radio Frequency Non-contact Vital Sign Detection," Proceedings of the 29th Annual International Conference of the IEEE EMBS, pp. 1651-1654, Lyon, France, Aug. 23-26, 2007, which is hereby incorporate by reference in its entirety.

Figure 3B:
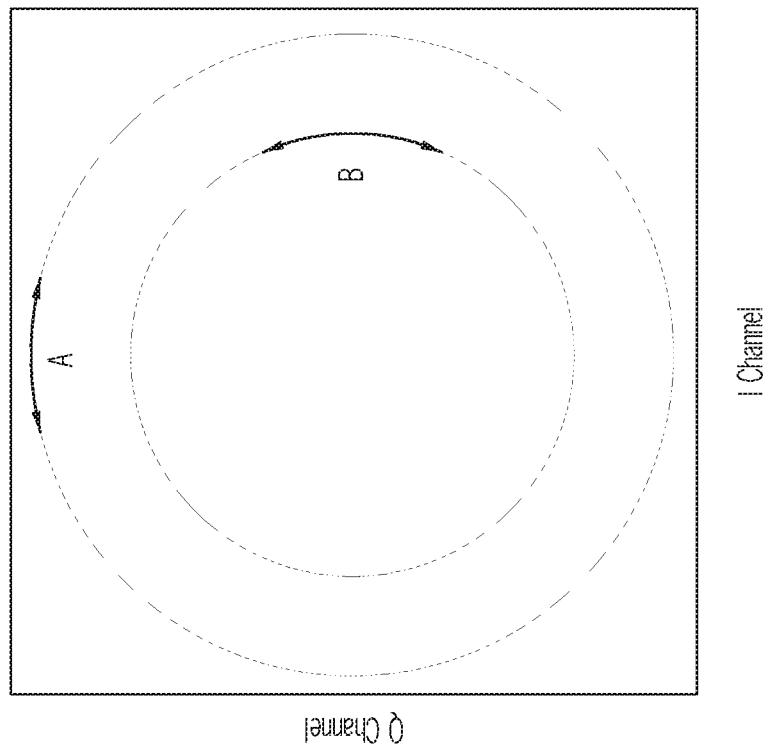
FIGS. 3A-3B show graphs illustrating.
Figure 3A:
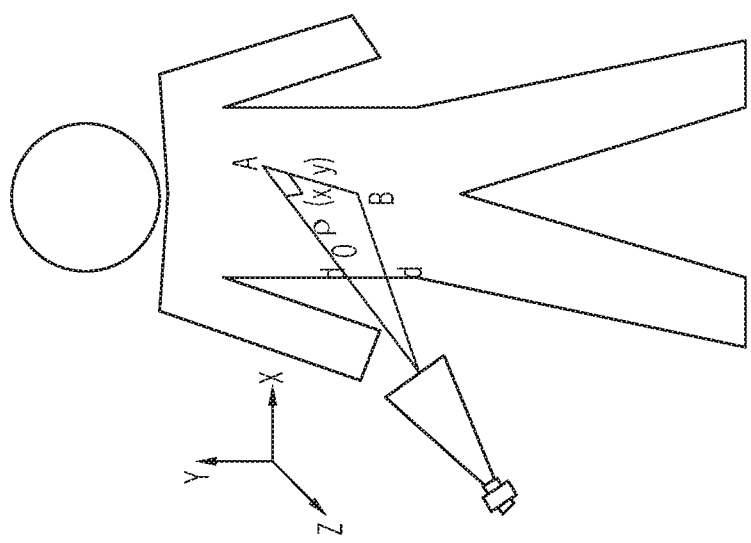

FIGS. 3A-3B show graphs illustrating: (FIG. 3A) ray-tracing model and the angular information (FIG. 3B) ray-tracing model of signals reflected from point A and B on the body using a 5.8 GHz radar, according to the present invention. The antenna is facing the body in the −Z direction of the X-Y-Z coordinate. As shown in FIG. 3 (FIG. 3A), the actual received signal should be represented from a ray-tracing point of view as:

$$I(t) = \int\int_s E(x, y) \cdot \cos\left[\left[\Delta\phi + \frac{4\pi}{\lambda}\{\rho(x, y)^2 + [d_0 + m_h(x, y)\sin(\omega_h t) + m_r(x, y)\sin(\omega_r t)]^2\}^{1/2}\right]\right] \times ds \quad (9.a)$$

-continued
$$Q(t) = \int\int_s E(x, y) \cdot \sin\left[\left[\Delta\phi + \frac{4\pi}{\lambda}\{\rho(x, y)^2 + [d_0 + m_h(x, y)\sin(\omega_h t) + m_r(x, y)\sin(\omega_r t)]^2\}^{1/2}\right]\right] \times ds. \quad (9.b)$$

Assume the antenna is placed 1 m away in front of the heart center, and the locations of the heart center A and the body center B on the front chest wall are separated by 11 cm. The difference in the transmission path for signals from the antenna to the two points is $\Delta x = \sqrt{1^2 + 0.11^2} - 1 = 0.006$ m, which is replicated in the receiving path and would produce a phase difference of 83.5 degree for a 5.8 GHz radar. Meanwhile, the radiation intensity of the antenna on the body surface is different from point to point, depending on the antenna radiation pattern. This implies that the received baseband signals from the two points will have different locations and movement patterns in the constellation graph, as shown in FIG. 3 (FIG. 3B). Therefore, the real case for vital sign detection using complex signal demodulation and arctangent demodulation is complicated by the phase offset. Numerical simulations are needed and will be presented in the following section.

IV. SIMULATION

Simulations have been performed based on the ray-tracing model. The two demodulation techniques were applied to vital sign detection in the presence/absence of random body movement.

A. Ray-Tracing Model

Figure 4A:
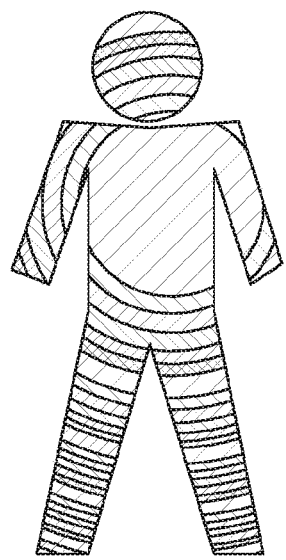
FIGS. 4A-4D show a ray-tracing model illustrating.
Figure 4B:
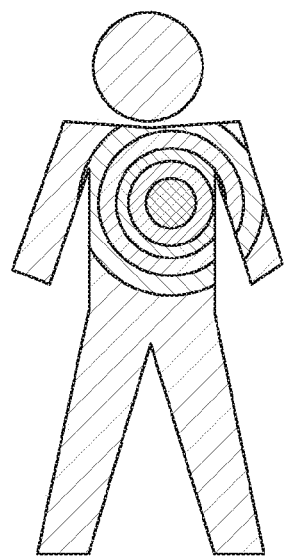
Figure 4C:
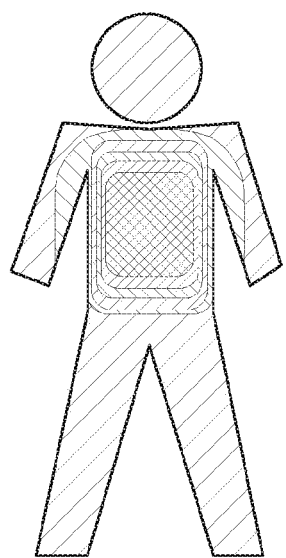
Figure 4D:
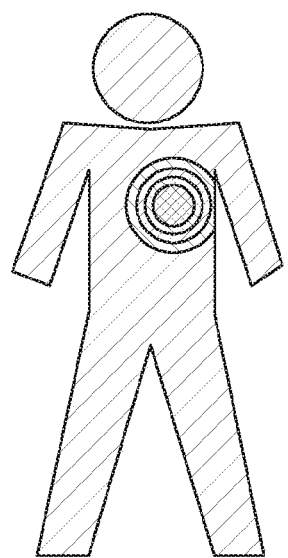

FIGS. 4A-4D. is a ray-tracing model illustrating: (FIG. 4A) the phase offset on the surface of human body radiated by a 5.8 GHz radar; (FIG. 4B) a 7 by 7 elements antenna array's radiation intensity on the human body; (FIG. 4C) approximation of the normalized amplitude of body movement caused by respiration; and (FIG. 4D) approximation of the normalized amplitude of body movement caused by heartbeat, according to the present invention. The body model for a subject of 1.8 m height is shown in FIG. 4A-4D. Assuming the antenna is 1 m in front of the heart center, the phase offset in different paths compared with the beam propagating to the center of the heart is shown in FIG. 4A for a 5.8 GHz radar sensor. Dramatic change in phase offset is observed. Shown in FIG. 4B is the radiation intensity on the human body produced by an ideal 7 by 7 antenna array comprised of omnidirectional antennas spaced by $\lambda/2$. FIGS. 4C and 4D are the approximation of the normalized amplitude of body movements caused by respiration and heartbeat, respectively. It can be inferred that when a carrier frequency of 24 GHz is used for the higher sensitivity at shorter wavelengths, the phase change will be more significant.

B. Demodulation without Random Body Movement

To demonstrate the properties of the two demodulation techniques, numerical simulations were first performed without random body movement present. Two examples are presented, i.e. a 5.8 GHz quadrature radar, and a 24 GHz quadrature radar. Three types of signals were recorded and analyzed.

Case I: a single-beam signal projected to the heart center, i.e. point A in FIG. 3A. This is the case analyzed by the single-beam model.

Case II: a single-beam signal projected to the body center, i.e. point B in FIG. 3A. In this case, respiration signal was picked up while heartbeat signal is almost absent.

Case III: the actual signal transmitted and received by the radar.

It should be noted that only Case III can be realized in the laboratory. Case I and II analyze signals carried by a hypothetical single beam radiated by an antenna with a very high directivity radiation pattern.

Example I: 5.8 GHz Quadrature Radar

Figure 5B:
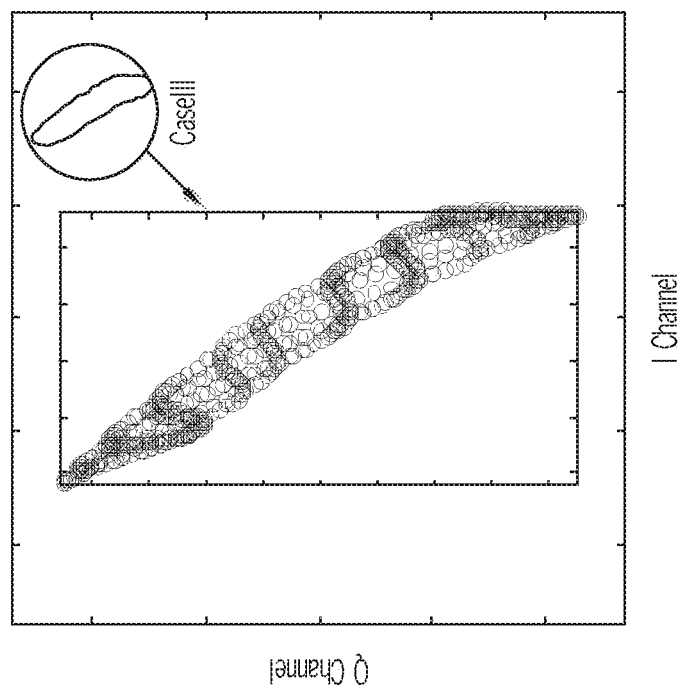
FIGS. 5A-5D show a graph of demodulation for a 5.8 GHz radar illustrating.
Figure 5A:
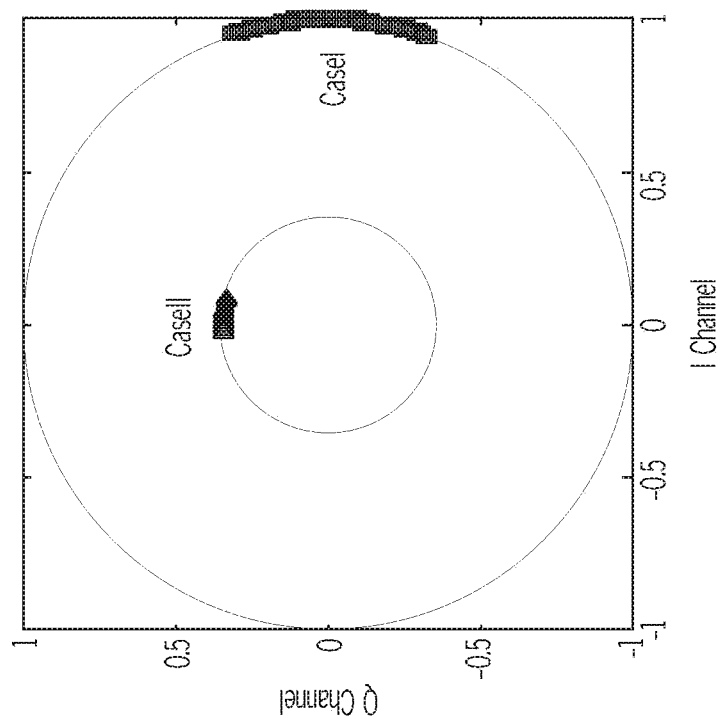

Simulation results are shown in FIGS. 5A-5D for detection from the back of the human body. More specifically FIGS. 5A-5B is a graph of demodulation for a 5.8 GHz radar illustrating: (FIG. 5A) a signal detected at heart center (Case I) and at body center (Case II); (FIG. 5B) an actual received signal (Case III); (FIG. 5C) an angular information $\psi(t)$ of the received signal; and (FIG. 5D) baseband spectra obtained by the complex signal demodulation and the arctangent demodulation (the DC component is not shown in the baseband spectrum). The residual phase produced in the electronic circuit was assumed to be 0°, which means the Q channel was at the optimum detection point while the I channel was at the null detection point according to the single-beam model.

FIGS. 5A-5B show the signal trajectories in the constellation graph. As predicted in Section II, signals reflected from different parts of the human body are affected by two variations: the phase offset and the radiation intensity. The former variation embodies itself as different angles of the trajectory shown in FIG. 5A, while the latter is demonstrated as different radii of the trajectory. As a result, when the receiver receives the vital sign signals, which is the superposition of all the signals reflected from different parts of the body, the total received signal trajectory is deformed from an ideal circle, as shown in FIG. 5B. It should be noted that the constellation deformation is not caused by noise, which was not included in simulation.

Figure 5C:
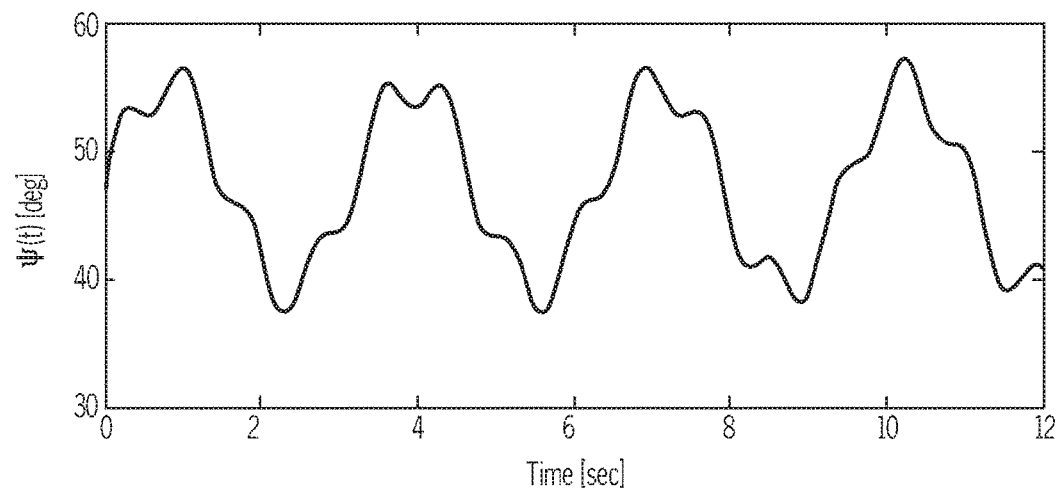
Figure 5D:
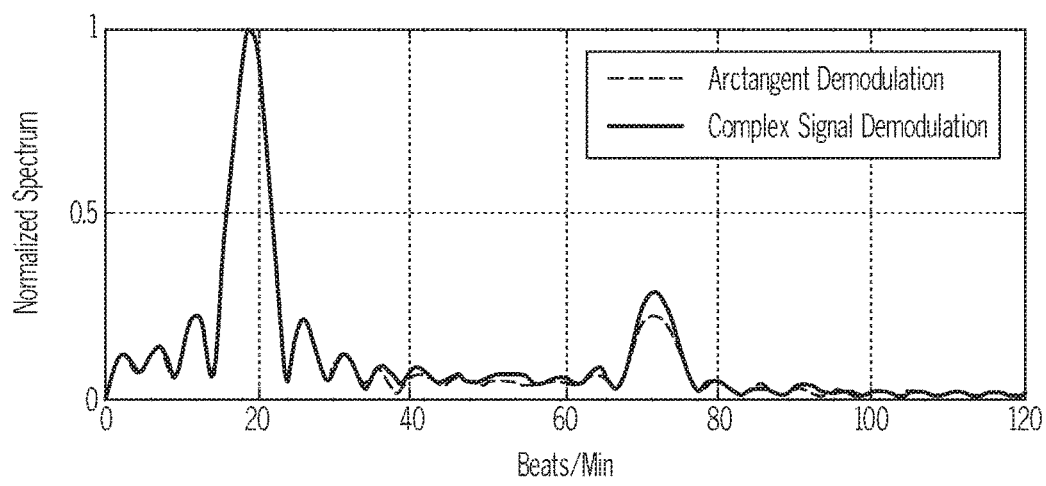

Although the foregoing discussions and simulation results appear undesirable, the recovered angular information based on equation (6) is nonetheless periodic and not seriously disturbed by the phase offset problem, as shown in FIG. 5C. The spectrum of the complex signal and the recovered angular information were analyzed and plotted in FIG. 5D. Although the detection was made with one channel at the null detection point and the other at the optimum detection point, both of the two demodulation techniques can successfully identify the respiration and heartbeat components.

Therefore, the complex signal demodulation and the arctangent demodulation for 5.8 GHz radar system are demonstrated to be effective solutions to achieve reliable detection and eliminate the null detection point problem.

Example II: 24 GHz Quadrature Radar

Figure 6B:
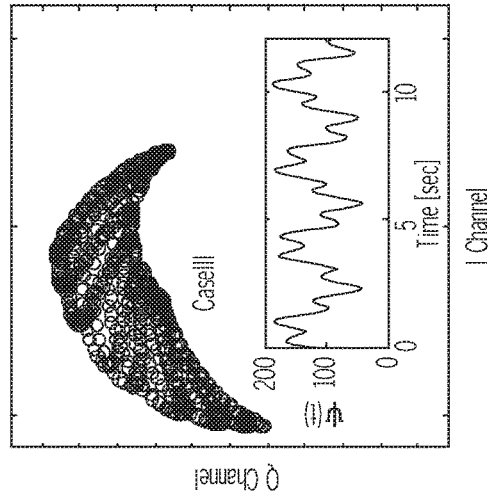
FIGS. 6A-6C show a graph of demodulation for a 24 GHz radar illustrating.
Figure 6A:
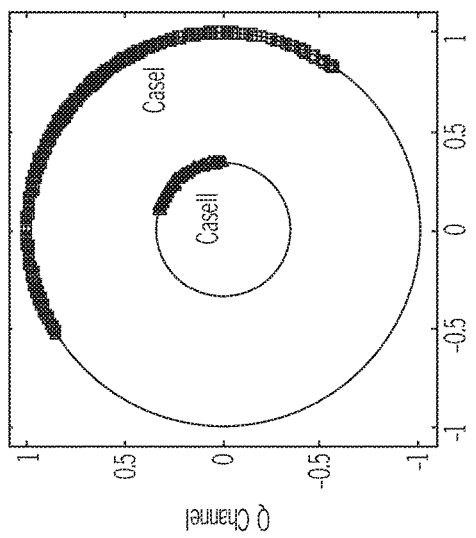
Figure 6C:
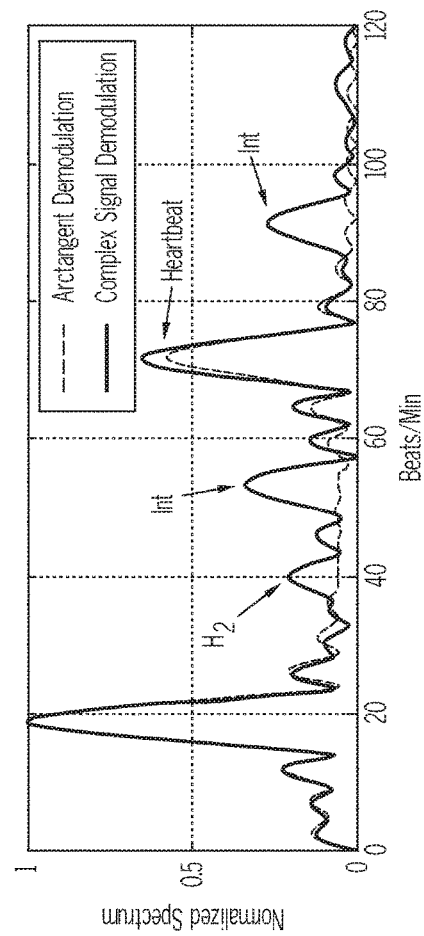

In this example, the carrier frequency was 24 GHz and the residual phase produced in the electronic circuit was assumed to be 450, which means the detection was performed at the middle between the null and the optimum detection points. The constellation plots are shown in FIGS. 6A-6C. More specifically, FIGS. 6A-6C are graphs of demodulation for a 24 GHz radar illustrating: (FIG. 6A) a signal detected at heart center (Case I) and at body center (Case II); (FIG. 6B) an actual received signal (Case III), with the recovered angular information shown in inset; (FIG. 6C) a baseband spectra obtained by the complex signal demodulation and the arctangent demodulation (DC component not shown in the spectra), according to the present invention. The complex signal demodulation causes harmonic ($H_2$) and intermodulation (Int) interference. Due to fast variation of the phase offset on the surface of the human body, more severe trajectory deformation was observed. However, angular information recovered from equation (6) is still periodic, as shown in the inset of FIG. 6B. The baseband spectra from the two demodulation techniques are shown in FIG. 6C. Again, the respiration and the heartbeat components can be identified from the spectrum by using both of the techniques.

Furthermore, the result in FIG. 6C verifies that the arctangent demodulation can eliminate the harmonics and intermodulation terms caused by the nonlinear phase modulation effect, making the spectrum cleaner than that obtained by complex signal demodulation.

Figure 7A:
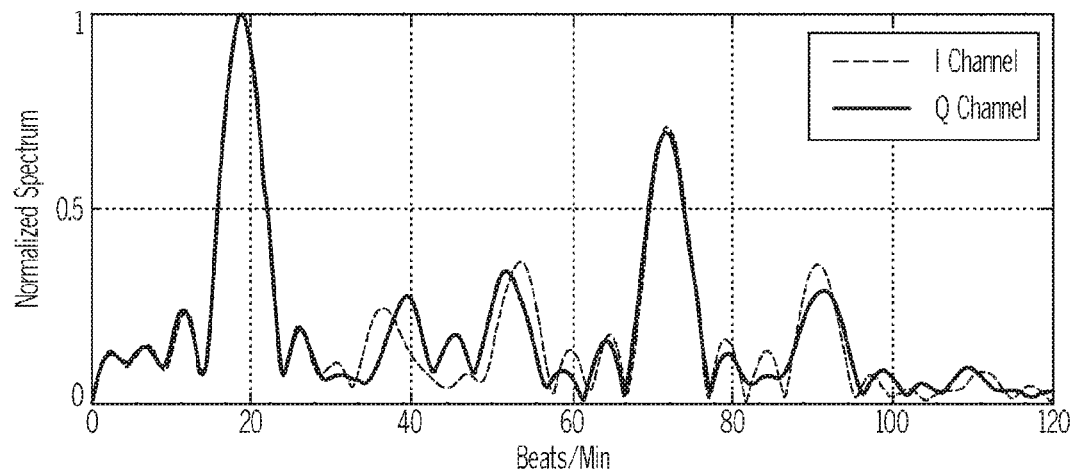
FIGS. 7A-7B show a graph of a baseband spectrum detected by the I and the Q channels with a carrier frequency of 24 GHz illustrating.
Figure 7B:
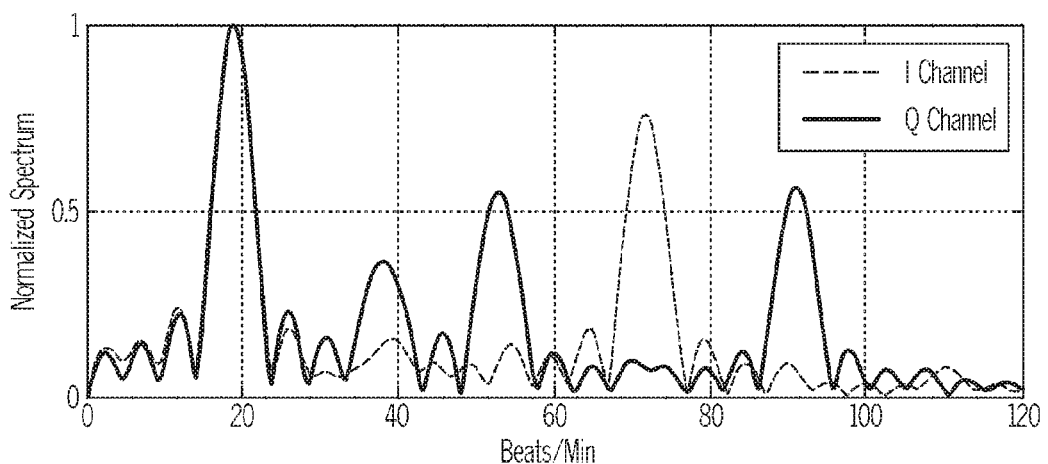

Another phenomenon to be noted is the optimum/null detection ambiguity. FIGS. 7A-7B is a graph of a baseband spectrum detected by the I and the Q channels with a carrier frequency of 24 GHz illustrating: (FIG. 7A) a spectrum of a single-beam signal projected to the heart center; and (FIG. 7B) a spectrum of the actually received signal, according to the present invention. Shown in FIG. 7A is the baseband spectrum of the I and the Q channels in Case I, i.e. the spectrum of the single beam signal projected to the center of the heart. The peaks of the respiration and the heartbeat components in I channel have the same amplitudes as those in Q channel, which is in accordance with equations (2.a) and (2.b) predicted by the single-beam model since the detection was performed at the mid-point between the null and the optimum detection points. However, the baseband spectrum of the actual received signal, as shown in FIG. 7B, shows that the I and the Q channels have significant differences in the heartbeat signal strength. While the I channel preserves the heartbeat signal, the Q channel shows strong harmonic and intermodulation components. This is because of the enhancement and cancellation among signals with different phase offsets. And it demonstrates the necessity of effectively combining the two channels even when the detection is not carried out at the null detection point.

C. Random Body Movement Cancellation

The random body movement cancellation technique was also simulated using the ray-tracing model with a carrier frequency of 5.8 GHz. The random roaming of the body was fully modeled in three dimensions (X, Y, and Z) which are defined in FIGS. 3A-3B. Typically the subject under test has larger random body movements in two dimensions than the third dimension, e.g. the horizontal movements in the X and Z directions are more obvious than the vertical movement in the Y direction for a seated person. Therefore, the time-variant velocity of random body movement was modeled as uniform distribution between 0 and a maximum value of 4 mm/s in the X and the Z directions. And the amplitude of random body movement in the Y direction was modeled as 0.1 of that in the other two directions.

Figure 8A:
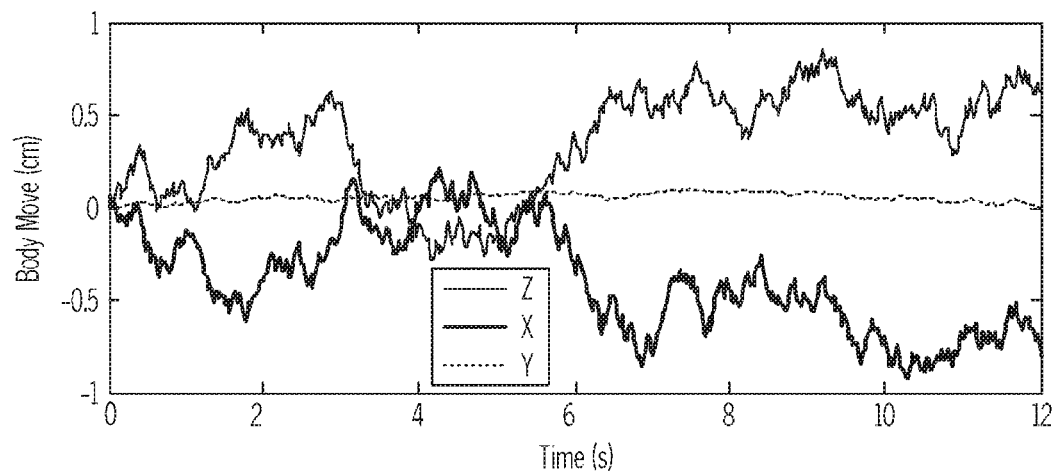
FIGS. 8A-8B show a graph of baseband spectra obtained when random body movement is present illustrating.
Figure 8B:
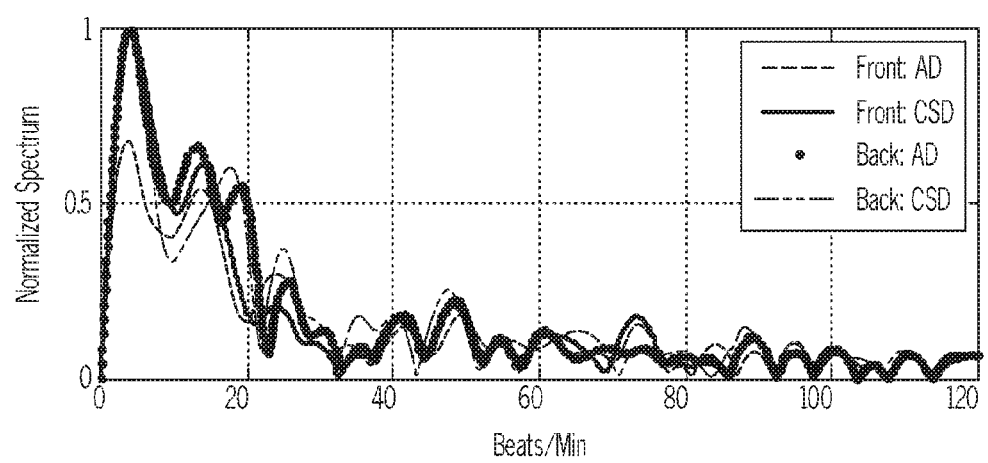

Turning now to FIGS. 8A-8B is a graph of baseband spectra obtained when random body movement is present illustrating: (FIG. 8A) the random body movement is shown in the Z, X, and Y directions, which are defined in FIGS. 3A-3B; and (FIG. 8B) a baseband spectra by arctangent demodulation (AD) and complex signal demodulation (CSD), according to the present invention. The movement components in each direction are shown in FIG. 8A, and the baseband spectra detected from the front and the back using the two demodulation techniques are shown in FIG. 8B. When random body movement is present, the desired respiration and heartbeat signal components will be overwhelmed by the noise generated by random body movement.

Figure 9A:
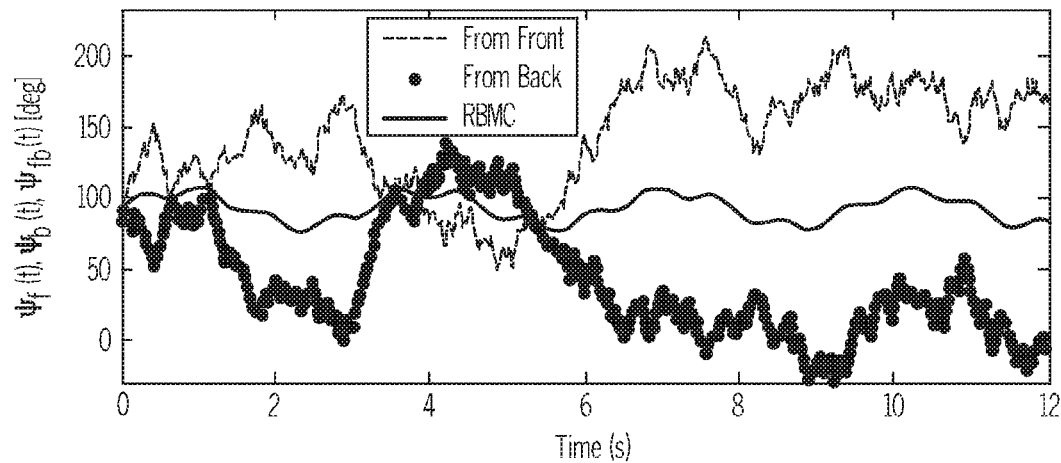
FIGS. 9A-9B show a graph of illustrating.
Figure 9B:
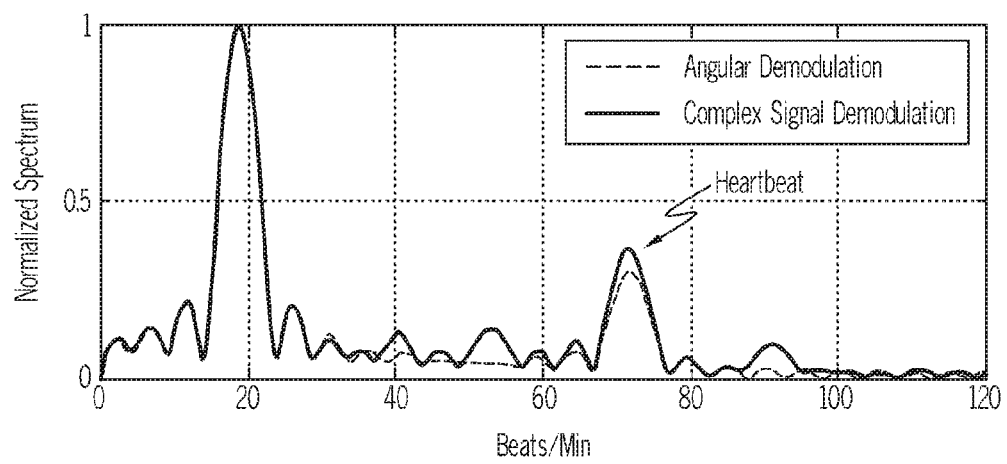

FIGS. 9A-9B show a graph illustrating: (FIG. 9A) angular information and baseband spectrum; and (FIG. 9B) angular information recovered by random body movement cancellation (RBMC) using the two demodulation techniques; accurate DC information is used in demodulation but not shown in the spectrum, according to the present invention. If the system can successfully preserve the DC offset information up to the baseband output, the recovered baseband angular information and the spectra obtained by random body movement cancellation were simulated and shown in FIGS. 9A-9B. The respiration and heartbeat components were successfully recovered by both demodulation techniques, which showed similar performance in recovering the desired signal components. It should be noted that although the random body movement can exist in the direction perpendicular to the radar direction, this technique still works reliably because only the movement in the radar direction is critical for the detection.

If the DC offset cannot be perfectly preserved up to the baseband output, however, the performance of random body movement cancellation based on both of the demodulation techniques deteriorates.

Figure 10A:
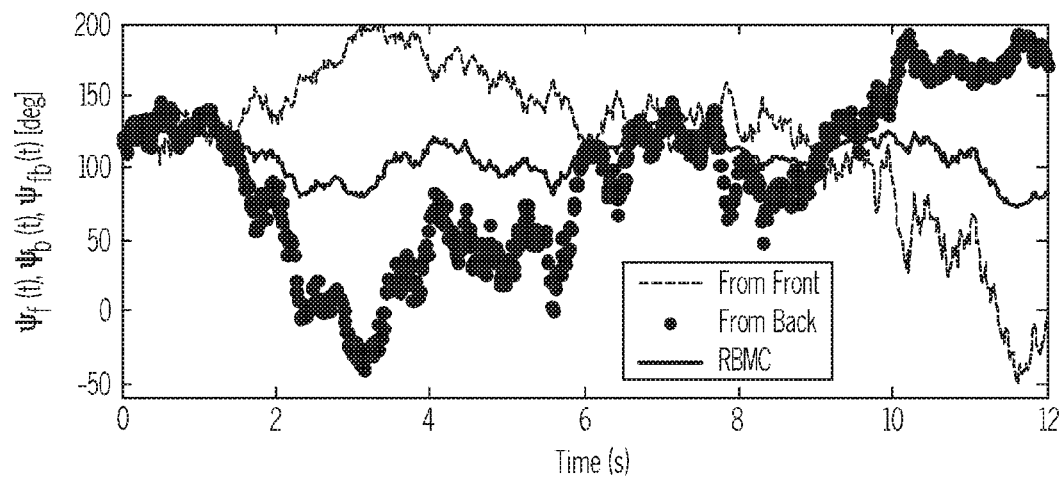
FIGS. 10A-10B show a graph illustrating.
Figure 10B:
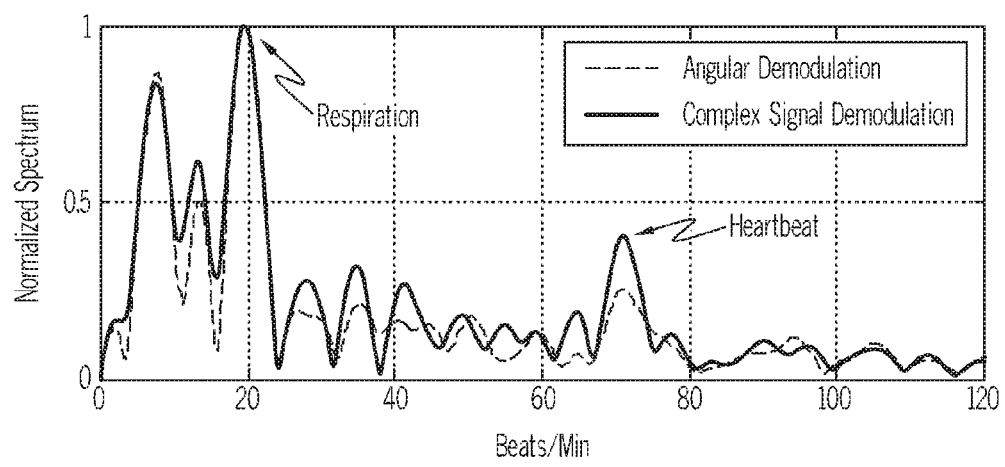

FIGS. 10A-10B show a graph illustrating: (FIG. 10A) angular information and baseband spectrum; and angular information recovered from the random body movement cancellation (RBMC) technique; the random body movements are modeled in three dimensions, and the DC offset in each transceiver is 30% of the maximum signal amplitude, according to the present invention. More specifically, shown in FIGS. 10A-10B is an example when DC offset was present at the baseband output of the two transceivers but not accurately preserved. For each transceiver, the baseband DC offset levels were modeled to be the same in the I/Q channels and were 30% of the maximum signal amplitude. In the simulation, the above DC offset level was subtracted from the ideal I and Q channel signals. Then, both demodulation techniques were applied to cancel out the random body movement. It is shown that the complex signal demodulation can still identify the respiration and heartbeat components, but the arctangent demodulation is unable to recover the heartbeat signal. The reason for this disadvantage of using arctangent demodulation in random body movement cancellation is, as shown in equation (8), the cancellation is based on the linear combination of the calculated phase, which is strongly affected by the location of the constellation origin.

V. EXPERIMENT

Figure 11:
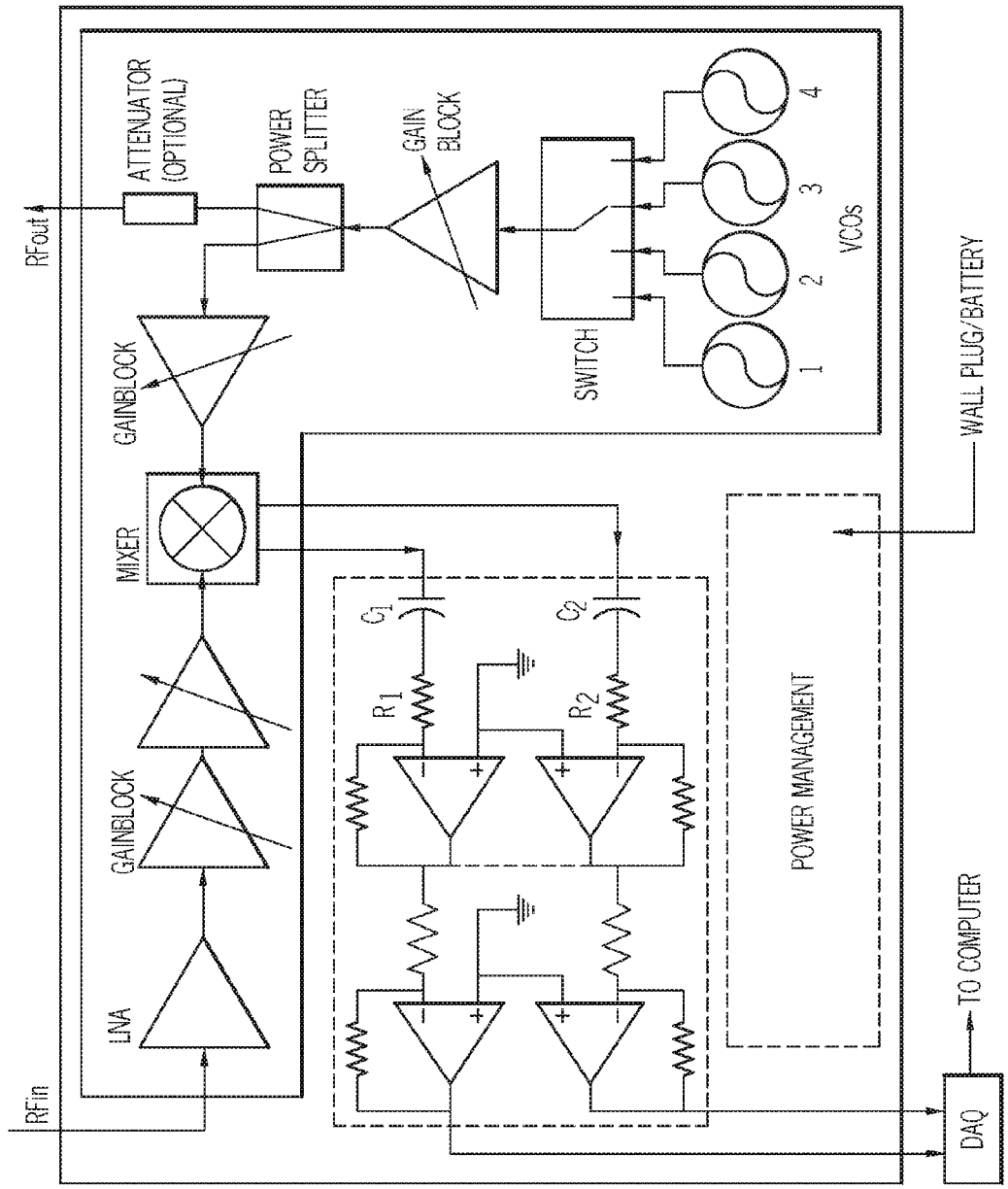
FIG. 11 is a block diagram of the 4-7 GHz radar transceiver as shown in FIG. 1, according to the present invention.

Experiments have been performed in the laboratory to verify the theory and compare the performance of the two demodulation techniques for random body movement cancellation. For consumer applications of this technique, it is desirable to have portable radars that can detect vital signs from several meters away, radiate a power of lower than 0 dBm, and have all the hardware integrated together at an affordable price. Therefore, 4-7 GHz portable radar was designed for this purpose. The radar integrates the quadrature transceiver, the two-stage baseband amplifier, and the power management circuit on a single printed circuit board (Rogers RO4350B substrate) with a size of 6.8×7.5 cm². FIG. 11 is a block diagram of the 4-7 GHz radar transceiver as shown in FIG. 1, according to the present invention. The specifications and manufacturers of the radio frequency components are listed in Table I. For research purpose, four voltage controlled oscillators (VCO) were implemented for a wide tuning range to obtain different optimal carrier frequencies under different environments. This is further described in the publication by Li, and J. Lin, "Optimal Carrier Frequency of Non-contact Vital Sign Detectors," Proceedings of IEEE Radio and Wireless Symposium, pp. 281-284, Long Beach, Jan. 9-11, 2007, which is hereby incorporate by reference in its entirety. When a specific application is known, only one VCO is needed and the SP4T switch can be eliminated to further reduce the cost.

TABLE I

BUILDING BLOCKS AND SPECIFICATIONS USED IN 4-7 GHZ RADAR

| Block | Manufacturer | Specifications |
|---|---|---|
| VCO1 | Hittite | 4.45-5.0 GHz, −105 dBc/Hz @100 kHz phase noise, 4 dBm output power |
| VCO2 | Hittite | 5.0-5.5 GHz, −103 dBc/Hz @100 kHz phase noise, 2 dBm output power |
| VCO3 | Hittite | 5.5-6.1 GHz, −102 dBc/Hz @100 kHz phase noise, 2 dBm output power |
| VCO4 | Hittite | 6.1-6.72 GHz, −101 dBc/Hz @100 kHz phase noise, 4.5 dBm output power |
| Switch | Hittite | DC-8 GHz, 40 dB isolation @6 GHz, 1.8 dB insertion loss @6 GHz, SP4T |
| Gain Block | RFMD | DC-8 GHz, 15.5 dB maximum gain, 14.5 dBm P1dB @6 Ghz |
| Mixer | Hittite | 4-8.5 GHz, 50 dB LO to RF isolation, 40 dB image rejection |
| LNA | Hittite | 3.5-7.0 GHz, 16 dB gain, 2.5 dB NF |

Since the vital sign has a frequency less than several Hertz, large coupling capacitors C1 and C2 of 10 μF were used to isolate the DC voltages of the mixer output and baseband amplifier input. Because the 10 μF coupling capacitors block the DC signal in addition to isolating DC voltages of two different circuits, no DC information was recorded during the measurement. The coupling capacitor (C1, C2=10 μF) and the baseband amplifier input resistor (R1, R2=160 ks) were chosen such that for a heartbeat signal with a frequency around 1 Hz, the voltage drop on the capacitor is no more than ⅒ of the signal amplitude. This leads to a time constant of approximately 1.6 seconds, which means that in the real-time signal processing software, a 2 second initiation time is needed.

For random body movement cancellation, measurements were performed by two identical radars. In this embodiment patch antenna arrays with orthogonal polarization were installed in the two transceivers to eliminate the interference between the two units. An example of these radars is further described in the publication by C. Li, and J. Lin, "Complex Signal Demodulation and Random Body Movement Cancellation Techniques for Non-contact Vital Sign Detection," *IEEE MTT-S International Microwave Symposium Digest*, June, 2008, which is hereby incorporated by reference in its entirety. It was observed in the experiment that the antenna gain should be higher than 4 dB for the radar to have a good signal-to-noise ratio from up to 2 m away. The antenna was designed to have a maximum directivity gain of 9 dB at broadside, so that the vital signs of the subject in front of the antenna will be picked up. Free-running VCOs were used for the two transmitters so that the actual carrier wavelengths were close to each other but always had a slight difference in the absence of a phase-locked-loop. As a result, the signal from one transceiver was further rejected by the other transceiver in the baseband because the small difference in the carrier frequency results in a large difference in baseband frequency compared to the vital sign frequencies. The phase noise reduction due to range correlation makes the free-running VCO adequate for vital sign detection. This is further described in the publication by A. D. Droitcour, O. Boric-Lubecke, V. M. Lubecke, J. Lin, and G. T. A. Kovac, "Range correlation and I/Q performance benefits in single-chip silicon Doppler radars for noncontact cardiopulmonary monitoring," IEEE Trans. Microwave Theory and Techniques, vol. 52, pp. 838-848, March 2004, which is hereby incorporate by reference in its entirety along with the publication by M. C. Budge, Jr. and M. P. Burt, "Range correlation effects on phase and amplitude noise," Proc. IEEE Southeastcon, Charlotte, N.C., 1993, pp 5, which is hereby incorporated by reference in its entirety.

To reduce the hardware cost and the requirement of signal processing speed, the amplified baseband signals were sampled by a 12-bit multifunction data acquisition module (NI USB-6008) with a low sampling rate of 20 Hertz, which is fast enough for the vital sign signal of typically less than 2.5 Hertz. The sampled data were fed into a laptop for real-time signal processing by LabVIEW. The sampling rate and resolution make it possible to implement the baseband signal processing in a low cost DSP microchip such as the TI C2000 family digital signal controllers for various applications in the future.

To focus on the properties of demodulation and random body movement cancellation techniques, no baseband filtering was implemented in either hardware or software. All the results presented are based on the original baseband signal.

A. DC Offset Estimation in Baseband

Because of the coupling capacitor in the radar between the receiver output and the baseband amplifier input and the variability of DC offset within the experimental environment, it is relatively difficult to accurately calibrate out the DC offset of the whole system. Instead, the DC offset was estimated by fitting the signal trajectory into a proper segment of circle in the constellation graph.

Figure 12A:
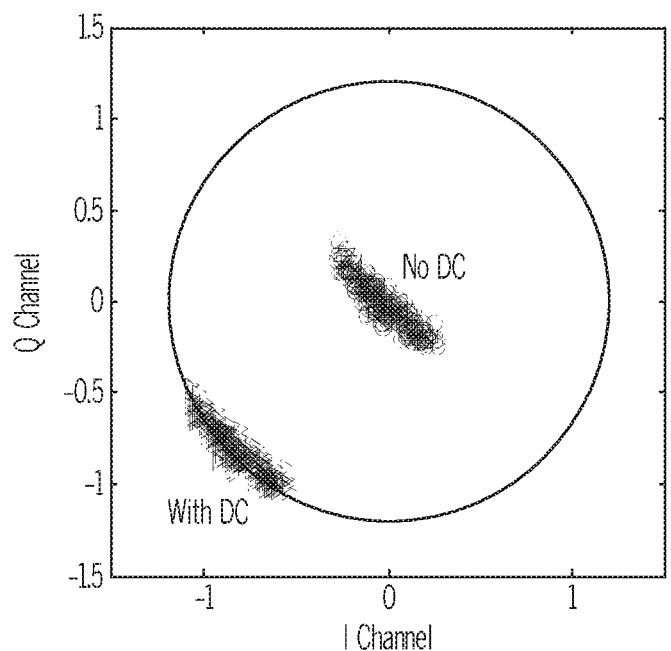
FIGS. 12A-12B show a graph of DC offset estimation illustrating.
Figure 12B:
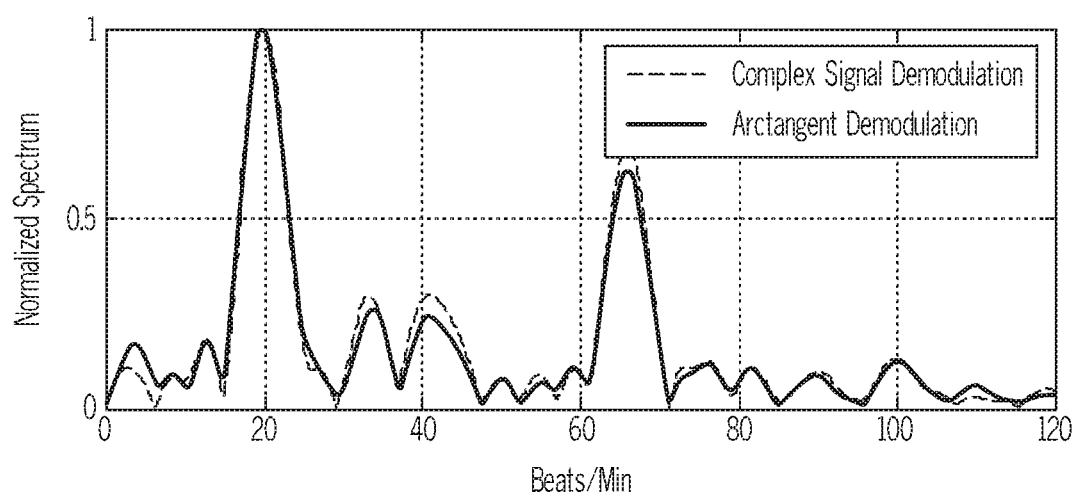

Turning now to FIGS. 12A-12B show a graph of DC offset estimation illustrating: (FIG. 12A) a trajectory of detected baseband signal with no DC information and with estimated DC offset level added; and (FIG. 12B) a spectra obtained by the two demodulation techniques. Signal with estimated DC offset added was used for arctangent demodulation. For example, FIG. 12A shows the constellation graph of the baseband signal detected from the back of the human body when no random body movement was present. Because of the absence of DC information, the original signal trajectory was located at the center of the constellation graph. After adding an estimated DC offset level of 0.8 V for both I and Q channels in the baseband, the trajectory was fitted into a circle. FIG. 12B shows the baseband spectra obtained by the complex signal demodulation and the arctangent demodulation. As shown in both theory and experiment in, the DC offset does not affect complex signal demodulation when random body movement is absent. This is described further in the publication by C. Li, and J. Lin, "Complex Signal Demodulation and Random Body Movement Cancellation Techniques for Non-contact Vital Sign Detection," IEEE MTT-S International Microwave Symposium Digest, June, 2008, which is hereby incorporate by reference in its entirety. Therefore, the spectrum obtained by complex signal demodulation can be used as a reference to evaluate the reliability of arctangent demodulation using the estimated DC offset information. The spectra of FIG. 12B match well with each other, showing that the baseband DC offset estimation method is accurate enough for arctangent demodulation when no random body movement is present. Based on this DC offset estimation method, estimated DC offsets were added to original detected data and used for random body movement cancellation. However, it should be noted that in the presence of the random body movement, the DC information produced by the reflection from the bulk of the body always changes. Therefore, it is impossible to dynamically obtain the precise DC offset information of the overall system: no matter whether the DC offset is calibrated out using the method proposed in the publication by B. Park, O. Boric-Lubecke, and V. M. Lubecke, "Arctangent demodulation with DC offset compensation in quadrature Doppler radar receiver systems", IEEE Trans. Microwave Theory and Techniques, vol. 55, pp. 1073-1079, May 2007, which is hereby incorporated by reference in its entirety, or estimated by the signal trajectory fitting method of this paper, there will always be DC information error when the body position changes. And it is of great interest to compare in real experiments that how robust the two demodulation techniques are in the presence of the inevitable DC offset error.

B. Random Body Movement Cancellation

Figure 13A:
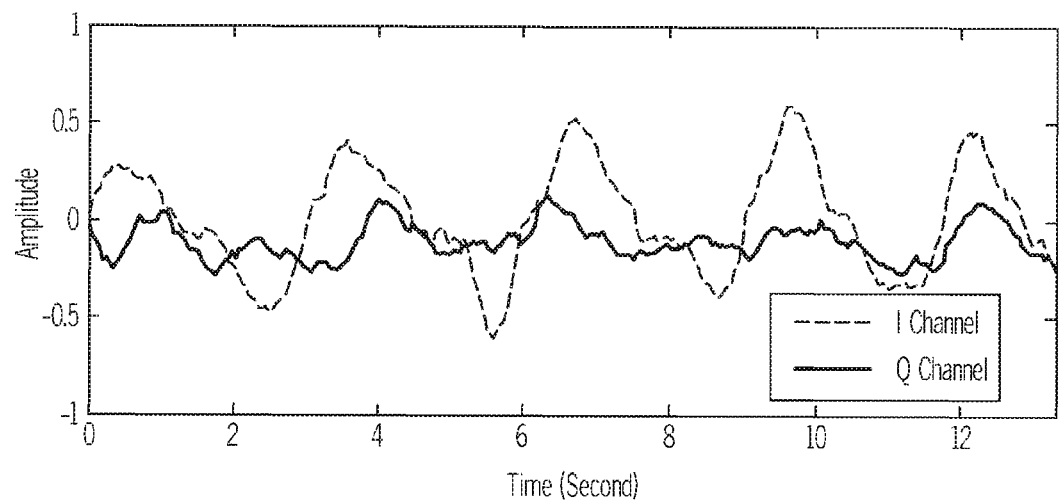
Figure 13B:
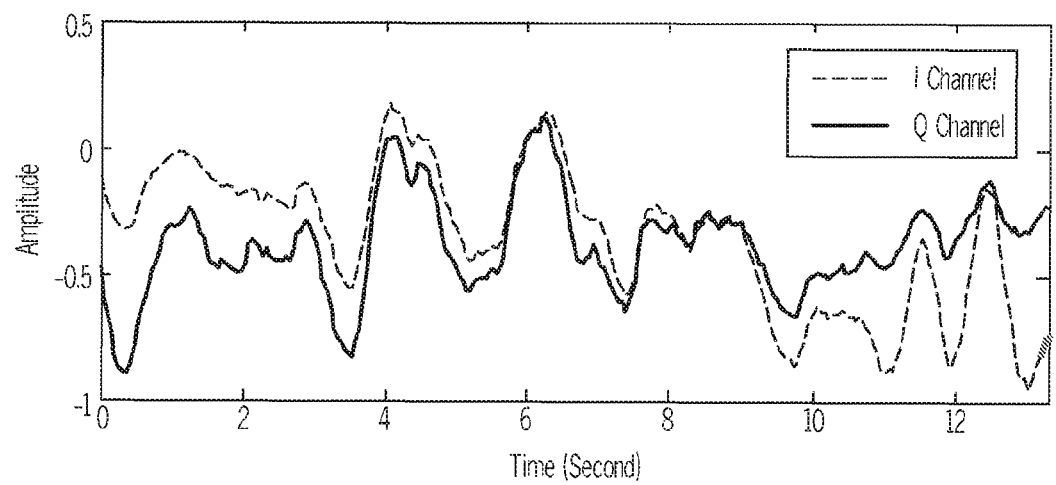

During the experiment, the subject under test was gently changing position in a chair, so that the noise of random body movement was emphasized. FIGS. 13A-13B show graphs of signals detected from: (FIG. 13A) the front of a human body; and (FIG. 13B) the back of the human body, according to the present invention. Further, FIGS. 13A-13B show the time domain signal detected from the front and the back of the human body when random body movement was present. Since the physiological movement caused by respiration and heartbeat has larger amplitude on the front chest wall than on the back, the signal detected from the back is more severely affected by the random body drift. Note that the detected signal amplitude shown in FIGS. 13A-13B do not reflect the real physiological movement amplitude, since other factors such as distance and baseband amplifier gain also affect the signal level. For example, in the experiment, the baseband amplifier gain of the radar detecting from the back is 3 dB higher than the other one detecting from the front. The two demodulation techniques were used to cancel out random body movement to recover the desired signal.

Figure 14A:
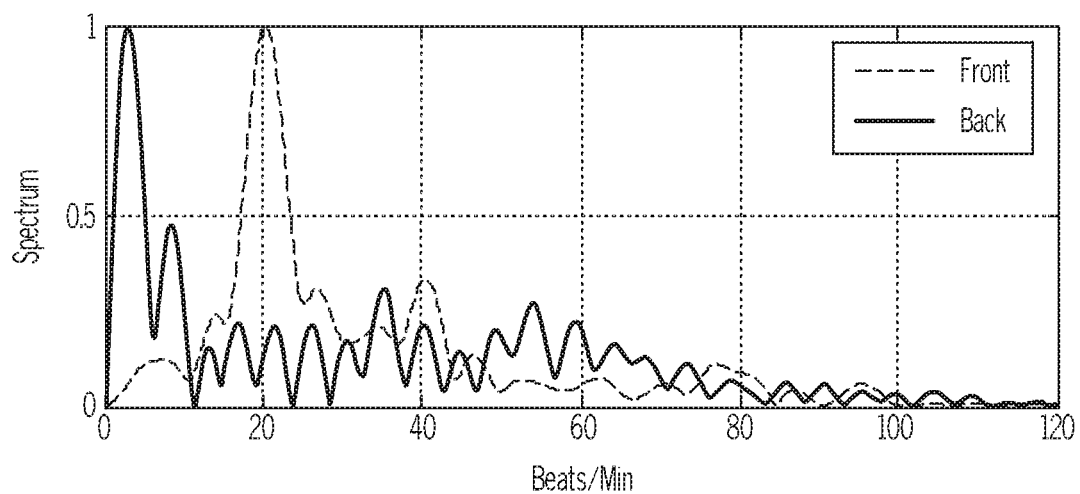
FIGS. 14A-14B show a graph of random body movement cancellation using arctangent demodulation illustrating.
Figure 14B:
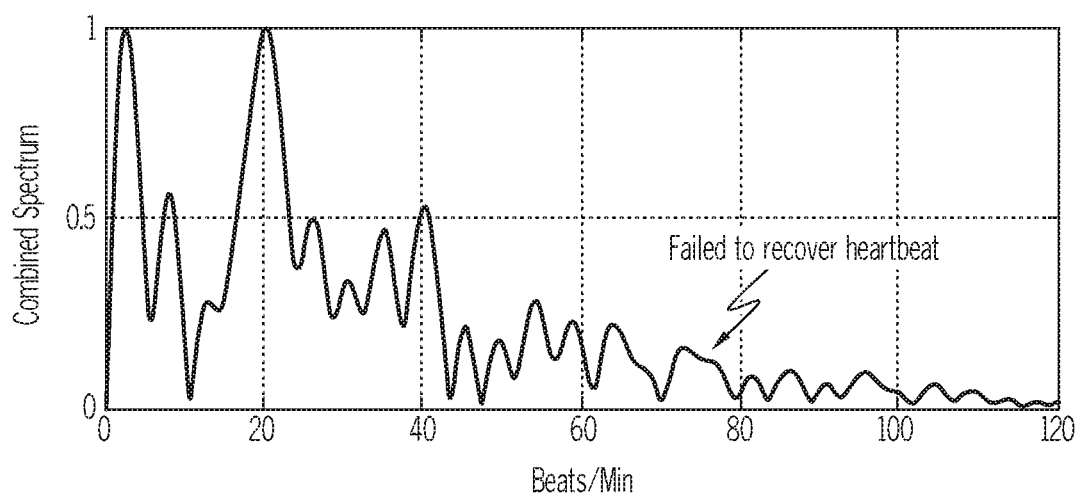

The estimation based on signal trajectory fitting was used here for arctangent demodulation. FIGS. 14A-14B show graphs of random body movement cancellation using arctangent demodulation illustrating: (FIG. 14A) a spectra measured from the front and the back of the human body; (FIG. 14B) a spectrum from combining the two transceiver outputs, the heartbeat information cannot be recovered due to inaccurate DC offset information, according to the present invention.

The baseband spectra detected from the front and the back of the human body are shown in FIG. 14A. The angular information from the two transceivers was combined as described in Section II-B, and the resulting baseband spectrum is shown in FIG. 14B. Due to the inaccuracy of DC offset estimation, the combined spectrum failed to recover the desired heartbeat signal component.

Figure 15A:
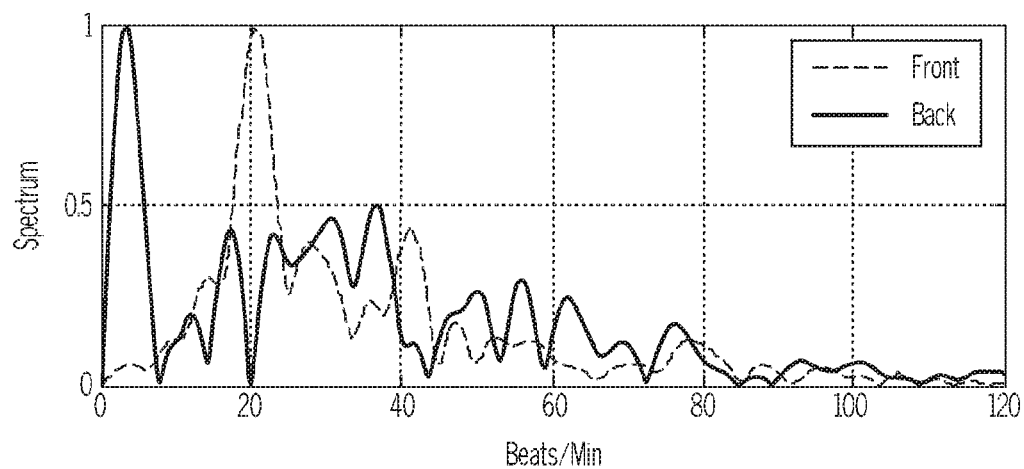
FIGS. 15A-15B show a graph of random body movement cancellation using complex signal demodulation illustrating.
Figure 15B:
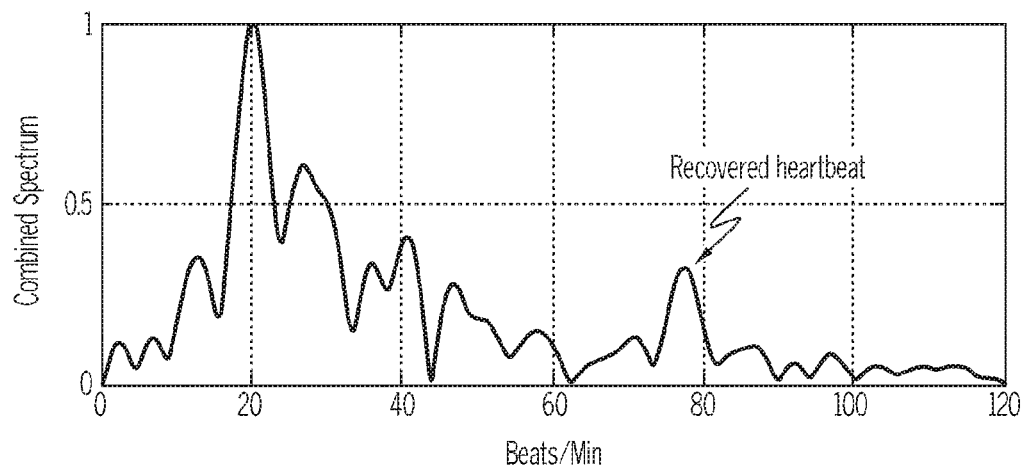

On the other hand, the same signals have been processed by the complex signal demodulation. FIGS. 15A-15B show graphs of random body movement cancellation using complex signal demodulation illustrating: (FIG. 15A) a spectra measured from the front and the back of the human body; and (FIG. 15B) an output spectrum by the random body movement cancellation technique, the heartbeat information is recovered, according to the present invention. This is further described in the publication by C. Li, and J. Lin, "Complex Signal Demodulation and Random Body Movement Cancellation Techniques for Non-contact Vital Sign Detection," IEEE MTT-S International Microwave Symposium Digest, June, 2008, which is hereby incorporated by reference in its entirety.

FIG. 15A shows the baseband spectra of the complex signal detected from the front and the back of the human body. Since the physiological movement at the back is weaker than that at the front chest wall, the noise completely overwhelmed the physiological signals from the back and only overwhelmed the heartbeat signal from the front. When the technique described in Section II-A was applied to combine the signals detected from the front and the back of the human body, the heartbeat signal was successfully recovered as shown in FIG. 15B.

The above comparative study verifies the simulation in Section IV-C that the complex signal demodulation is more favorable in random body movement cancellation when the DC offset at baseband output cannot be accurately determined.

VI. CONCLUSION AND NON-LIMITING EXAMPLES

Simulations and experiments have been performed to demonstrate the complex signal demodulation and the arctangent demodulation for random body movement cancellation in Doppler radar vital sign detection. The complex signal demodulation is easier to implement in that it does not need an intermediate signal processing stage to recover the angular information, and it is robust when DC offset is present. The latter property also makes it more favorable for random body movement cancellation. On the other hand, the arctangent demodulation has the advantage of eliminating the harmonic and intermodulation interference at high frequencies using high gain antennas. The effects of constellation deformation and optimum/null detection ambiguity caused by the phase offset due to finite antenna directivity are also discussed.

The present invention can be realized in hardware, software, or a combination of hardware and software. A system according to a preferred embodiment of the present invention can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general purpose computer system with a computer program that, when being loaded and executed, controls the computer system such that it carries out the methods described herein.

In general, the routines executed to implement the embodiments of the present invention, whether implemented as part of an operating system or a specific application, component, program, module, object or sequence of instructions may be referred to herein as a "program." The computer program typically is comprised of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 16:
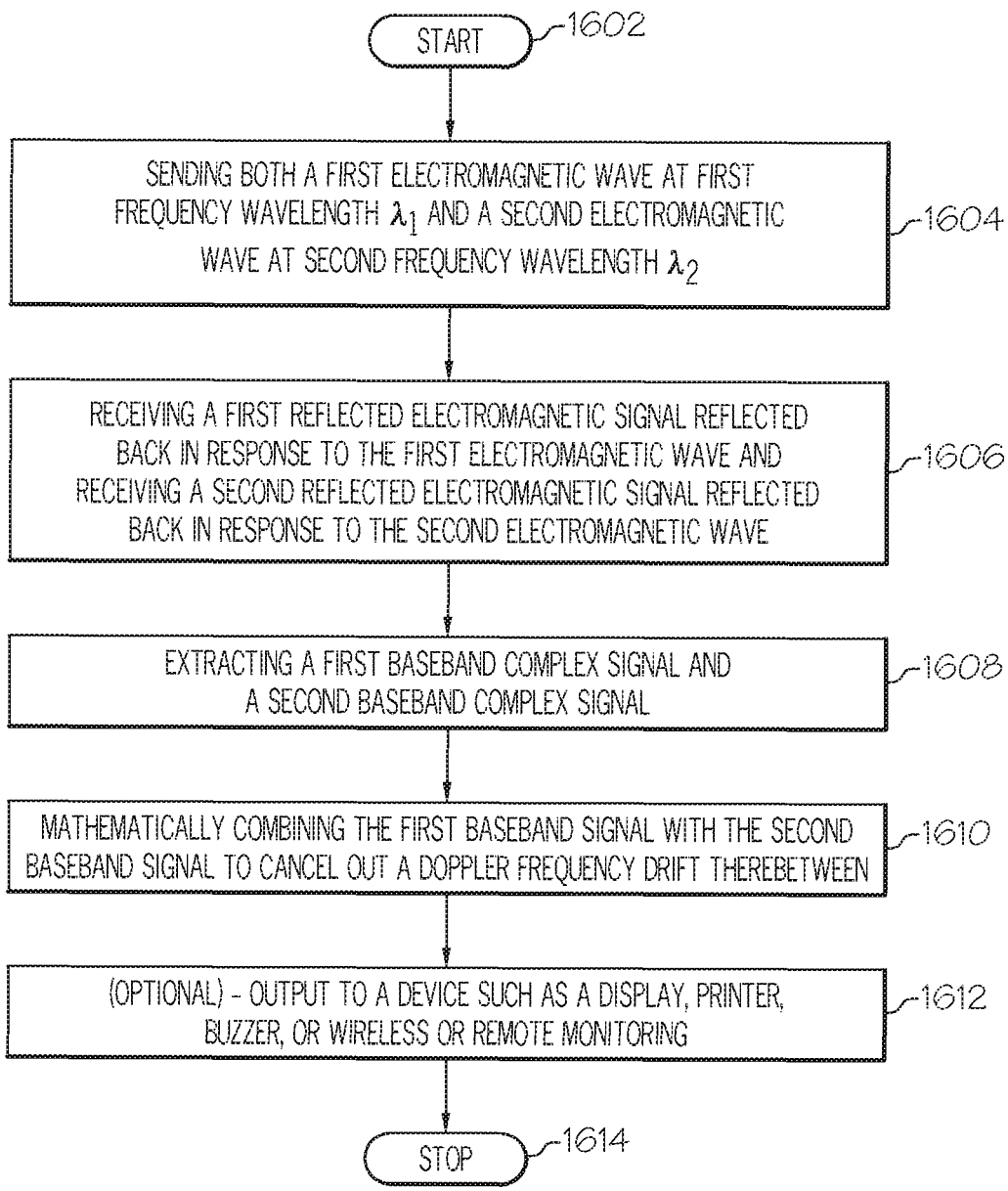
FIG. 16 is a flow diagram of the overall random body movement cancellation, according to the present invention.

FIG. 16 is a flow diagram of the overall random body movement cancellation, according to the present invention. The process begins in step 1602 and immediately proceeds to step 1604 with sending on at least two electromagnetic signals comprising a first electromagnetic signal with a first frequency to a first side of a body from a first electromagnetic wave transceiver and a second electromagnetic signal with a second frequency to a second side of a body from a second electromagnetic wave transceiver. Next in step 1606 these signals are received. In step 1608, a first baseband signal and a second baseband signal are extracted out of the first electromagnetic signal and the second electromagnetic signal respectively In step 1610 a demodulation is carried out by mathematically combining the first baseband complex signal with the second baseband complex signal to cancel out a Doppler frequency drift therebetween to yield a periodic Doppler phase effect. An optional step 1612 is performed for output the results to a device such as a display, printer, buzzer, storage or wireless device and the process ends in step 1614.

Figure 17:
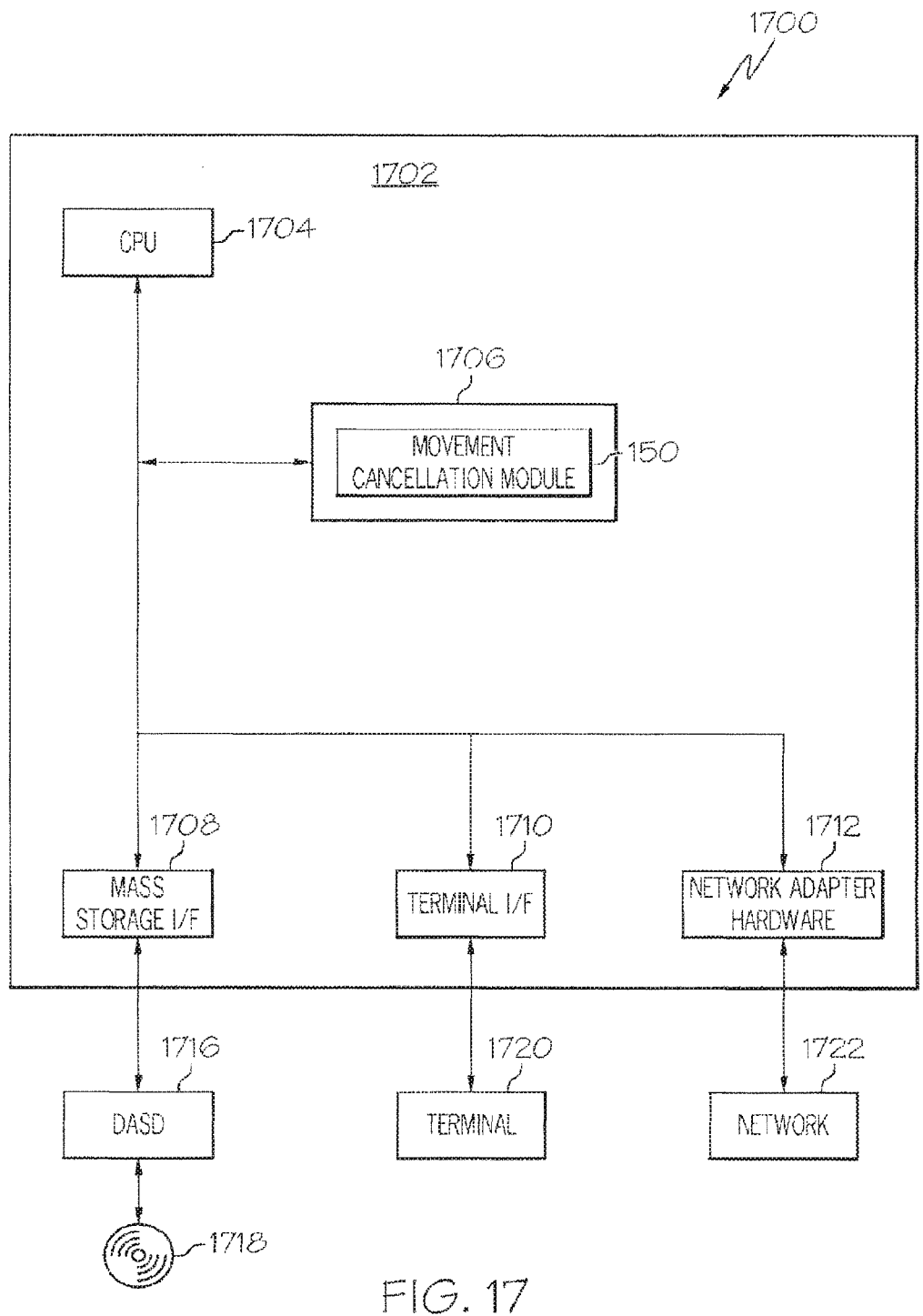
FIG. 17 is a generalized block diagram of a computer system useful for implementing the noise cancellation algorithm according to the present invention.

FIG. 17 is a generalized block diagram 1700 of a computer system useful for implementing the noise cancellation algorithm according to the present invention. The mass storage interface 1708 is used to connect mass storage devices, such as data storage device 1716, to the information processing system 1700. One specific type of data storage device is a computer readable medium such as DASD drive 1716, which may be used to store data to and read data from a CD 1718. The main memory 1706 comprises the movement cancellation module 150, which has been discussed above in greater detail. Although illustrated as concurrently resident in the main memory 1706, it is clear that respective component(s) of the main memory 1706 are not required to be completely resident in the main memory 1706 at all times or even at the same time.

Although only one CPU 1704 is illustrated for computer 1702, computer systems with multiple CPUs can be used equally effectively. Embodiments of the present invention further incorporate interfaces that each includes separate, fully programmed microprocessors that are used to off-load processing from the CPU 1704. Terminal interface 1710 is used to directly connect one or more terminals 1720 to computer 1702 to provide a user interface to the computer 1702. These terminals 1720, which are able to be non-intelligent or fully programmable workstations, are used to allow system administrators and users to communicate with the information processing system 1700. The terminal 1720 is also able to consist of user interface and peripheral devices that are connected to computer 1702 and controlled by terminal interface hardware included in the terminal I/F 1710 that includes video adapters and interfaces for keyboards, pointing devices, and the like.

An operating system (not shown) included in the main memory is a suitable multitasking operating system such as the Linux, UNIX, Windows, operating system. Embodiments of the present invention are able to use any other suitable operating system. Some embodiments of the present invention utilize architectures, such as an object oriented framework mechanism, that allows instructions of the components of operating system (not shown) to be executed on any processor located within the information processing system 1700. The network adapter hardware 1712 is used to provide an interface to the network 1722. Embodiments of the present invention are able to be adapted to work with any data communications connections including present day analog and/or digital techniques or via a future networking mechanism.

Although the exemplary embodiments of the present invention are described in the context of a fully functional computer system, those skilled in the art will appreciate that embodiments are capable of being distributed as a program product via CD or DVD, e.g. CD 1718, CD ROM, or other form of recordable media, or via any type of electronic transmission mechanism.

Further, even though a specific embodiment of the invention has been disclosed, it will be understood by those having skill in the art that changes can be made to this specific embodiment without departing from the spirit and scope of the invention. The scope of the invention is not to be restricted, therefore, to the specific embodiment, and it is intended that the appended claims cover any and all such applications, modifications, and embodiments within the scope of the present invention.

The invention claimed is:

1. A method for cancelling body movement effect for non-contact vital sign detection, comprising:

sending a first electromagnetic signal with a first frequency to a first side of a body from a first transceiver and a second electromagnetic signal with a second frequency to a second side of the body from a second transceiver, where the first frequency of wavelength $\lambda_1$ and the second frequency of wavelength $\lambda_2$ are close to each other so that $(\lambda_1 \approx \lambda_2 \approx \lambda)$;

receiving at least a first reflected electromagnetic signal reflected back in response to the first electromagnetic signal via the first transceiver and receiving at least a second reflected electromagnetic signal reflected back in response to the second electromagnetic signal via the second transceiver;

generating an angular information output by combining a first angular information signal extracted from the first reflected electromagnetic signal with a second angular information signal extracted from the second reflected electromagnetic signal to cancel out a Doppler frequency drift therebetween, where the first and second angular information signals are combined by arctangent demodulation as expressed by:

$$\psi_f(t) = \frac{4\pi x_{h1}(t)}{\lambda} + \frac{4\pi x_{r1}(t)}{\lambda} + \frac{4\pi y(t)}{\lambda} + \phi_1 \text{ and}$$

$$\psi_b(t) = \frac{4\pi x_{h2}(t)}{\lambda} + \frac{4\pi x_{r2}(t)}{\lambda} + \frac{4\pi y(t)}{\lambda} + \phi_2,$$

where $x_{h1}(t)$ and $x_{r1}(t)$ are heartbeat-induced and respiration-induced physiological movements on the first side of the body, $x_{h2}(t)$ and $x_{r2}(t)$ are heartbeat-induced and respiration-induced physiological movements on the second side of the body, $\phi_1$, $\phi_2$ are residual phases of the first transceiver and the second transceiver, and y(t) is a body movement, where the y(t) term in the angular information output $\psi_{fb}(t) = \psi_f(t) + \psi_b(t)$ is cancelled out by adding $\psi_f(t)$ and $\psi_b(t)$, while terms of physiological movement $x_{h1}(t)$, $x_{h2}(t)$, $x_{r1}(t)$ and $x_{r2}(t)$ are enhanced as expressed by:

$$\psi_{fb}(t) = \frac{4\pi[x_{h1}(t) + x_{h2}(t)]}{\lambda} + \frac{4\pi[x_{r1}(t) + x_{r2}(t)]}{\lambda} + \phi_1 + \phi_2;$$

and displaying a vital sign of the body extracted from the angular information output.

2. The method of claim 1, further comprising extracting at least one of respiration rate and heart rate from the angular information output.

3. The method of claim 2, further comprising sending the at least one of the respiration rate and the heart rate to a display.

4. The method of claim 2, further comprising sending the at least one of the respiration rate and the heart rate to a wireless output device for display.

5. The method of claim 1, wherein a DC offset of in-phase (I) and quadrature (Q) baseband components of at least one of the first and second reflected electromagnetic signals is calibrated out.

6. The method of claim 1, wherein a DC offset associated with at least one of the first and second reflected electromagnetic signals is calibrated using a trajectory-fitting procedure.

7. The method of claim 1, wherein the first transceiver and the second transceiver are anyone of:
   5.8 GHz quadrature radar transceivers; and
   24 GHz quadrature radar transceivers.

8. The method of claim 1, wherein the first and second angular information signals are based upon corresponding in-phase (I) and quadrature (Q) baseband components of the first and second reflected electromagnetic signals.

9. The method of claim 1, wherein the first side is a front of the body and the second side is a back of the body.

10. A system for cancelling body movement effect for non-contact vital sign detection, comprising:

a first transceiver configured to send a first electromagnetic signal with a first frequency to a first side of a body and receive a first reflected electromagnetic signal reflected back in response to the first electromagnetic signal;

a second transceiver configured to send a second electromagnetic signal with a second frequency to a second side of the body, where the first frequency and the second frequency are different frequencies, and receive a second reflected electromagnetic signal reflected back in response to the second electromagnetic signal, where the first frequency of wavelength $\lambda_1$ and the second frequency of wavelength $\lambda_2$ are close to each other so that $(\lambda_1 \approx \lambda_2 \approx \lambda)$;

a processing system configured to generate an angular information output by combining a first angular information signal extracted from the first reflected electromagnetic signal with a second angular information signal extracted from the second reflected electromagnetic signal to cancel out a Doppler frequency drift therebetween, where the first and second angular information signals are combined by arctangent demodulation as expressed by:

$$\psi_f(t) = \frac{4\pi x_{h1}(t)}{\lambda} + \frac{4\pi x_{r1}(t)}{\lambda} + \frac{4\pi y(t)}{\lambda} + \phi_1 \text{ and}$$

$$\psi_b(t) = \frac{4\pi x_{h2}(t)}{\lambda} + \frac{4\pi x_{r2}(t)}{\lambda} + \frac{4\pi y(t)}{\lambda} + \phi_2,$$

where $x_{h1}(t)$ and $x_{r1}(t)$ are heartbeat-induced and respiration-induced physiological movements on the first side of the body, $x_{h2}(t)$ and $x_{r2}(t)$ are heartbeat-induced and respiration-induced physiological movements on the second side of the body, $\phi_1$, $\phi_2$ are residual phases of the first transceiver and the second transceiver, and y(t) is a body movement, where the y(t) term in the angular information output $\psi_{fb}(t)=\psi_f(t)+\psi_b(t)$ is cancelled out by adding $\psi_f(t)$ and $\psi_b(t)$, while terms of physiological movement $x_{h1}(t)$, $x_{h2}(t)$, $x_{r1}(t)$ and $x_{r2}(t)$ are enhanced as expressed by:

$$\psi_{fb}(t) = \frac{4\pi[x_{h1}(t) + x_{h2}(t)]}{\lambda} + \frac{4\pi[x_{r1}(t) + x_{r2}(t)]}{\lambda} + \phi_1 + \phi_2;$$

and display a vital sign of the body extracted from the angular information output.

11. The system of claim 10, wherein the processing system is further configured to extract at least one of respiration rate and heart rate from the angular information output.

12. The system of claim 11, further comprising a display that displays the at least one of the respiration rate and the heart rate.

13. The system of claim 11, wherein the at least one of the respiration rate and the heart rate is communicated to a wireless output device for display.

14. The system of claim 11, wherein the at least one of the respiration rate and the heart rate is communicated to a storage device for subsequent access.

15. The system of claim 11, wherein a DC offset of in-phase (I) and quadrature (Q) baseband components of at least one of the first and second reflected electromagnetic signals is calibrated out.

16. The system of claim 10, wherein a DC offset associated with at least one of the first and second reflected electromagnetic signals is calibrated using a trajectory-fitting procedure.

17. The system of claim 10, wherein the first transceiver and the second transceiver are anyone of:
   5.8 GHz quadrature radar transceivers; and
   24 GHz quadrature radar transceivers.

18. The system of claim 10, wherein the first and second angular information signals are based upon corresponding in-phase (I) and quadrature (Q) baseband components of the first and second reflected electromagnetic signals.

19. The system of claim 18, wherein the I and Q baseband components are sampled by a digital acquisition module for subsequent processing.

20. The system of claim 10, wherein the first side is a front of the body and the second side is a back of the body.

\* \* \* \* \*